United States Patent
Sherman et al.

(10) Patent No.: US 12,353,975 B2
(45) Date of Patent: *Jul. 8, 2025

(54) APPARATUS AND METHOD FOR PERFORMING A LOCALIZATION OF A MOVABLE TREATMENT DEVICE

(71) Applicant: Braun GmbH, Kronberg (DE)

(72) Inventors: Faiz Feisal Sherman, Mason, OH (US); Xiaole Mao, Mason, OH (US)

(73) Assignee: Braun GmbH, Kronberg (DE)

( * ) Notice: Subject to any disclaimer, the term of this patent is extended or adjusted under 35 U.S.C. 154(b) by 1834 days.

This patent is subject to a terminal disclaimer.

(21) Appl. No.: 16/277,024

(22) Filed: Feb. 15, 2019

(65) Prior Publication Data

US 2019/0254796 A1    Aug. 22, 2019

(30) Foreign Application Priority Data

Feb. 19, 2018   (EP) ..................................... 18157358
Feb. 19, 2018   (EP) ..................................... 18157362

(51) Int. Cl.
*G06N 3/044*   (2023.01)
*A46B 15/00*   (2006.01)
(Continued)

(52) U.S. Cl.
CPC ......... *G06N 3/044* (2023.01); *A46B 15/0073* (2013.01); *A61C 17/22* (2013.01);
(Continued)

(58) Field of Classification Search
CPC ........ A46B 15/0006; A46B 2200/1066; G06F 18/256
See application file for complete search history.

(56) References Cited

U.S. PATENT DOCUMENTS 7,835,999 B2   11/2010   Block
7,877,338 B2   1/2011    Tani
(Continued)

FOREIGN PATENT DOCUMENTS

CN   101367015 A   2/2009
CN   102265242 A   11/2011
(Continued)

OTHER PUBLICATIONS

All Office Actions, U.S. Appl. No. 16/276,993.
(Continued)

*Primary Examiner* — Lam S Nguyen
(74) *Attorney, Agent, or Firm* — Jay A. Krebs; Jason J. Camp

(57) ABSTRACT

An apparatus for performing a localization of a movable treatment device having at least one inertial sensor and configured to treat the target surface. The apparatus has a motion pattern classification device configured to discriminate between two or more motion classes contained in a set of motion classes, and an interface for providing, from the inertial sensor to the motion pattern classification device, inertial sensor data representing a movement of the movable treatment device. The motion pattern classification device has a neural network configured to receive and classify inertial sensor data with respect to the motion classes associated with one or more different zones relating to the target surface so that the classification of inertial sensor data indicates an estimation of the location of the movable treatment device with respect to the one or more zones of the target surface.

14 Claims, 12 Drawing Sheets

(51) Int. Cl.
*A61C 17/22* (2006.01)
*A61C 17/26* (2006.01)
*G06F 16/28* (2019.01)
*G06N 3/08* (2023.01)
*G06V 40/20* (2022.01)
*G08B 21/18* (2006.01)
*A61C 17/16* (2006.01)
*A61C 17/34* (2006.01)
*B26B 21/40* (2006.01)

(52) U.S. Cl.
CPC ............ *A61C 17/221* (2013.01); *A61C 17/26* (2013.01); *G06F 16/285* (2019.01); *G06N 3/08* (2013.01); *G06V 40/20* (2022.01); *G08B 21/18* (2013.01); *A46B 15/0002* (2013.01); *A46B 15/0036* (2013.01); *A46B 15/0038* (2013.01); *A46B 15/004* (2013.01); *A46B 15/0071* (2013.01); *A46B 2200/1066* (2013.01); *A61B 2562/0219* (2013.01); *A61B 2562/0247* (2013.01); *A61B 2562/0252* (2013.01); *A61C 17/16* (2013.01); *A61C 17/3409* (2013.01); *B26B 21/4056* (2013.01); *B26B 21/4081* (2013.01); *G06F 2218/16* (2023.01)

(56) References Cited

U.S. PATENT DOCUMENTS

| | | |
|---|---|---|
| 8,175,840 B2 | 5/2012 | Hwang et al. |
| 8,251,821 B1 | 8/2012 | Yen et al. |
| 8,554,707 B2 | 10/2013 | Schäfer |
| 9,144,476 B2 | 9/2015 | Iwahori |
| 9,263,036 B1 | 2/2016 | Graves |
| 9,292,102 B2 | 3/2016 | Nasiri et al. |
| 9,646,244 B2 | 5/2017 | Corrado |
| 9,820,233 B2 | 11/2017 | Pakzad et al. |
| 11,755,686 B2 | 9/2023 | Sherman |
| 2003/0036835 A1 | 2/2003 | Breed et al. |
| 2005/0219213 A1 | 10/2005 | Cho et al. |
| 2008/0077326 A1 | 3/2008 | Funk et al. |
| 2008/0102953 A1 | 5/2008 | Schultz |
| 2008/0174550 A1 | 7/2008 | Laurila et al. |
| 2009/0092955 A1 | 4/2009 | Hwang |
| 2010/0145654 A1* | 6/2010 | Hwang ............ A46B 15/0006 706/15 |
| 2011/0010875 A1 | 1/2011 | Iwahori et al. |
| 2011/0060706 A1 | 3/2011 | Suzuki |
| 2014/0065588 A1 | 3/2014 | Jacobson et al. |
| 2014/0349256 A1 | 11/2014 | Connor |
| 2015/0109202 A1 | 4/2015 | Ataee et al. |
| 2015/0189008 A1 | 7/2015 | Krkkinen et al. |
| 2015/0316383 A1 | 11/2015 | Donikian |
| 2016/0073886 A1 | 3/2016 | Connor |
| 2016/0091308 A1 | 3/2016 | Oliaei |
| 2016/0091965 A1 | 3/2016 | Wang |
| 2016/0143718 A1 | 5/2016 | Serval |
| 2016/0235357 A1 | 8/2016 | Ohmer |
| 2017/0069203 A1* | 3/2017 | Vetter .................. G06F 18/256 |
| 2017/0173262 A1 | 6/2017 | Veltz |
| 2017/0176213 A1 | 6/2017 | Eriksson |
| 2017/0281054 A1 | 10/2017 | Stever et al. |
| 2017/0318954 A1 | 11/2017 | Nishiura et al. |
| 2018/0049001 A1 | 2/2018 | Volozh et al. |
| 2018/0125623 A1 | 5/2018 | Serval et al. |
| 2018/0168462 A1 | 6/2018 | Pernu |
| 2018/0250108 A1 | 9/2018 | Tamminga et al. |
| 2018/0284745 A1 | 10/2018 | Cella et al. |
| 2019/0005355 A1 | 1/2019 | Joyce et al. |
| 2019/0083215 A1 | 3/2019 | Serval et al. |
| 2019/0200746 A1 | 7/2019 | Serval et al. |
| 2019/0254794 A1 | 8/2019 | Sherman et al. |
| 2019/0254795 A1 | 8/2019 | Sherman et al. |
| 2019/0278786 A1 | 9/2019 | Sherman et al. |
| 2020/0089214 A1 | 3/2020 | Cella et al. |
| 2020/0320184 A1 | 10/2020 | Nikitidis et al. |
| 2020/0371491 A1 | 11/2020 | Wong |
| 2021/0153989 A1 | 5/2021 | Huang et al. |
| 2023/0211515 A1 | 7/2023 | Blatter |
| 2023/0342423 A1 | 10/2023 | Sherman et al. |

FOREIGN PATENT DOCUMENTS

| | | |
|---|---|---|
| CN | 104848861 A | 8/2015 |
| CN | 105832315 A | 8/2016 |
| CN | 106922185 A | 7/2017 |
| CN | 107092894 A | 8/2017 |
| CN | 107153642 A | 9/2017 |
| CN | 107203753 | 9/2017 |
| CN | 109002189 A | 12/2018 |
| CN | 107516102 B | 10/2020 |
| DE | 4218600 A1 | 12/1993 |
| EP | 3336648 A1 | 6/2018 |
| EP | 3528172 A2 | 8/2019 |
| JP | 2002090267 A | 3/2002 |
| JP | 2009240759 A | 10/2009 |
| JP | 2017187850 A | 10/2017 |
| JP | 2021513415 A | 5/2021 |
| KR | 20130057688 * | 6/2013 |
| KR | 20130057688 A | 6/2013 |
| WO | 2010024697 A1 | 3/2010 |
| WO | 2014089119 A1 | 6/2014 |
| WO | 2017042673 A1 | 3/2017 |
| WO | 2017165231 A1 | 9/2017 |
| WO | 2019081937 A1 | 5/2019 |

OTHER PUBLICATIONS

Partial European Search Report and Search Opinion; Application Ser. No. 19157585.1; dated Jul. 9, 2019; 17 pages.
Partial European Search Report and Search Opinion; Application Ser. No. 18157362.7; dated Sep. 10, 2018; 16 pages.
Extended European Search Report and Search Opinion; Application Ser. No. 19157585.1; dated Dec. 10, 2019; 19 pages.
International Search Report and Written Opinion; Application Ser. No. PCT/IB2019/051249; dated Sep. 18, 2019; 21 pages.
International Search Report and Written Opinion; Application Ser. No. PCT/IB2019/051248; dated Sep. 11, 2019; 22 pages.
Marcon, et al., "Smart Toothbrushes: Inertial Measurement Sensors Fusion with Visual Tracking", In Proceedings of European Conference on Computer Vision, Oct. 8, 2016, pp. 480-494.
Gravina, et al., "Multi-sensor fusion in body sensor networks: State-of-the-art and research challenges", In Journal of Information Fusion, vol. 35, May 2017, pp. 68-80.
Alex Graves, Abdel-rahman Mohamed and Geoffrey Hinton; "Speech Recognition With Deep Recurrent Neural Networks"; Department of Computer Science, University of Toronto; Mar. 22, 2013.
European Search Report with written opinion, mail date Oct. 4, 2018, 15 pages.
Dzung Tri Nguyen et al: "SwallowNet: Recurrent neural network detects and characterizes eating patterns", 2017 IEEE International Conference on Pervasive Computing and Communications Workshops (PERCOM Workshops), IEEE, Mar. 13, 2017 (Mar. 13, 2017), pp. 401-406, XP033092320,DOI: 10.1109/PERCOMW.2017. 7917596[retrieved on May 2, 2017]* II.B, IV, V *.
Hssayeni Murtadha D et al: "Automatic assessment of medication states of patients with Parkinson's disease usingwearable sensors", 2016 38th Annual International Conference of the IEEE Engineering in Medicine Andbiology Society (EMBC), IEEE, Aug. 16, 2016 (Aug. 16, 2016), pp. 6082-6085, XP032980553, DOI: 10.1109/ EMBC.2016.7592116[retrieved on Oct. 13, 2016].
Langkvist Martin et al: "A review of unsupervised feature learning and deep learning for time-series modeling", Pattern Recognition Letters, vol. 42, Jun. 1, 2014 (Jun. 1, 2014), pp. 11-24, XP028831931, ISSN: 0167-8655, DOI: 0.1016/J.PATREC.2014.01.008 * 3.5 and Figure 4 *.
Ming Zeng, Le T. Nguyen, Bo Yu, Ole J. Mengshoel, Jiang Zhu, Pang Wu, Joy Zhang; "Convolutional Neural Networks for Human

(56) References Cited

OTHER PUBLICATIONS

ActivityRecognition using Mobile Sensors"; 2014 6th International Conference on Mobile Computing, Applications and Services (MobiCASE).

Natalia Neverova, Christian Wolf, Griffin Lacey, Lex Fridman, Deepak Chandra, Brandon Barbello, Graham Taylor; "Learning Human Identity from Motion Patterns"; Apr. 21, 2016.

Nicholas D. Lane, Petko Georgiev; "Can Deep Learning Revolutionize Mobile Sensing?" HotMobile'15, Feb. 12-13, 2015, Santa Fe, NM, USA.

Yousaf Saeed et al: "A Sensor-Augmented Golf Club", a Dissertation submitted to the University of Dublin.

Young-Jae Lee et al: "Toothbrushing Region Detection Using Three-Axis Accelerometer and Magnetic Sensor", IEEE Transactions on Biomedical Engineering, IEEE, USA, vol. 59, No. 3, Mar. 1, 2012 (Mar. 1, 2012), pp. 872-881, XP011490011, ISSN: 0018-9294, DOI: 10.1109/TBME.2011.2181369.

All Office Actions; U.S. Appl. No. 16/276,972, filed Feb. 15, 2019.
All Office Actions; U.S. Appl. No. 16/276,947, filed Feb. 15, 2019.
All Office Actions; U.S. Appl. No. 18/215,248, filed Jun. 28, 2023.
Inoue, et al., "Deep Recurrent Neural Network for Mobile Human Activity Recognition with High Throughput", In Repository of arXiv:1611.03607, Nov. 11, 2016, 10 pages.

Khan, et al., "A Triaxial Accelerometer-Based Physical-Activity Recognition via Augmented-Signal Features and a Hierarchical Recognizer", In Journal of IEEE Transactions on Information Technology in Biomedicine, vol. 14, Issue 5, Sep. 2010, pp. 1166-1172.

Wang, et al., "Human Activity Recognition with User-Free Accelerometers in the Sensor Networks", In Proceedings of the International Conference on Neural Networks and Brain, Oct. 13, 2005, pp. 1212-1217.

* cited by examiner

Discriminating between two or more motion classes ($15_1$, $15_2$, $15_3$, ..., $15_k$) contained in a set (15) of motion classes of the movable treatment device (11)

↓ 801

Receiving at least one inertial sensor data ($17_1$) from an inertial sensor (13), the at least one inertial sensor data ($17_1$) representing a movement of the movable treatment device (11)

↓ 802

Receiving and processing by means of a neural network (18) the at least one inertial sensor data ($17_1$) and mapping the at least one inertial sensor data ($17_1$) to at least one motion class ($15_1$, $15_2$, $15_3$, ..., $15_k$) contained in the set (15) of motion classes, wherein said motion classes ($15_1$, $15_2$, $15_3$, ..., $15_k$) contained in the set (15) of motion classes are each associated with one or more different zones ($21_1$, $21_2$, $21_3$, ..., $21_m$) of the target surface (12) so that the mapping of the at least one inertial sensor data ($17_1$) with the at least one motion class ($15_1$, $15_2$, $15_3$, ..., $15_k$) indicates an estimation of the location of the movable treatment device (11) with respect to the one or more zones ($21_1$, $21_2$, $21_3$, ..., $21_m$) of the target surface (12)

APPARATUS AND METHOD FOR PERFORMING A LOCALIZATION OF A MOVABLE TREATMENT DEVICE

FIELD OF THE INVENTION

The present invention relates to an apparatus for performing a localization of a movable treatment device, a method for performing a localization of a movable treatment device and a system comprising the apparatus and the movable treatment device.

BACKGROUND OF THE INVENTION

Movable treatment devices may be used for treating a surface or the like. For instance, movable treatment devices may concern personal appliances such as a hair brush, a razor, a groomer, a toothbrush, or the like. In these examples, a surface to be treated may be a body or at least a certain portion or zone of said body.

Other examples of movable treatment devices may, for instance, concern household appliances such as a broom, a mop, a scrubbing brush or the like. In these examples, a surface to be treated may be a floor or at least a certain portion or zone of said floor.

In some applications it might be useful to know the current position of the movable treatment device. In some applications it might be useful to additionally or alternatively classify the motions of the movable treatment device, particularly in the case of a personal appliance.

Nowadays, imaging techniques may be used for localizing movable treatment devices with respect to a target surface by means of a camera capturing said target surface, for instance. It may also be known to use sensors, such as GPS sensors or the like, for localizing a movable treatment device. The aforementioned imaging techniques may also be used for imaging a motion of a movable treatment device and to classify said captured motion.

These common devices and methods may work suitably well for coarse localization and classification. However, several drawbacks may exist. For example, GPS sensors may only work sufficiently well in outdoor conditions. The field of view of a camera capturing a target surface may be obstructed, sometimes even by the movable treatment device itself. Furthermore, even if different users are using the movable treatment device, e.g. the personal appliance, the output of the above-mentioned devices and methods will always be the same for each user even though each user may have individual styles and preferences how to use said movable treatment device.

Thus, it would be desirable to provide apparatuses and methods that allow for a precise localization of a movable treatment device and/or a precise classification of motions of a movable treatment device without the above-mentioned drawbacks. Furthermore, it would be desirable to personalize these apparatuses and methods by providing individually trained techniques for different persons.

SUMMARY OF THE INVENTION

In accordance with one aspect an apparatus for performing a localization of a movable treatment device relative to a target surface is provided, the movable treatment device comprising at least one inertial sensor and being configured to treat the target surface, the apparatus comprising a motion pattern classification device configured to discriminate between two or more motion classes contained in a set of motion classes of the movable treatment device, and an interface for providing at least one inertial sensor data from the inertial sensor to the motion pattern classification device, the at least one inertial sensor data representing a movement of the movable treatment device, wherein the motion pattern classification device comprises at least one neural network configured to receive the at least one inertial sensor data and to classify the at least one inertial sensor data with respect to the motion classes contained in the set of motion classes, wherein said motion classes are each associated with one or more different zones relating to the target surface so that the classification of the at least one inertial sensor data with respect to the motion classes indicates an estimation of the location of the movable treatment device with respect to the one or more zones of the target surface.

In accordance with one aspect a method is provided for performing a localization of a movable treatment device relative to a target surface, the movable treatment device comprising at least one inertial sensor and being configured to treat the target surface, the method comprising providing two or more motion classes contained in a set of motion classes of the movable treatment device, receiving at least one inertial sensor data from the inertial sensor, the at least one inertial sensor data representing a movement of the movable treatment device, receiving and processing by means of a neural network the at least one inertial sensor data and classifying the at least one inertial sensor data with respect to at least one motion class contained in the set of motion classes, wherein the motion classes are each associated with one or more different zones of the target surface so that the classification of the at least one inertial sensor data with the at least one motion class indicates an estimation of the location of the movable treatment device with respect to the one or more zones of the target surface.

In accordance with one aspect a computer-readable digital storage medium is provided having stored thereon a computer program having a program code for performing, when running on a computer, the above-mentioned method for performing a localization of a movable treatment device relative to a target surface.

In accordance with one aspect, a system is provided that comprises a movable treatment device and an apparatus as previously described.

BRIEF DESCRIPTION OF THE DRAWINGS

In the following, embodiments of the present invention are described in more detail with reference to the figures, in which FIG. 8 shows a block diagram of an inventive method according to an embodiment.

DETAILED DESCRIPTION OF THE INVENTION

Figure 1:
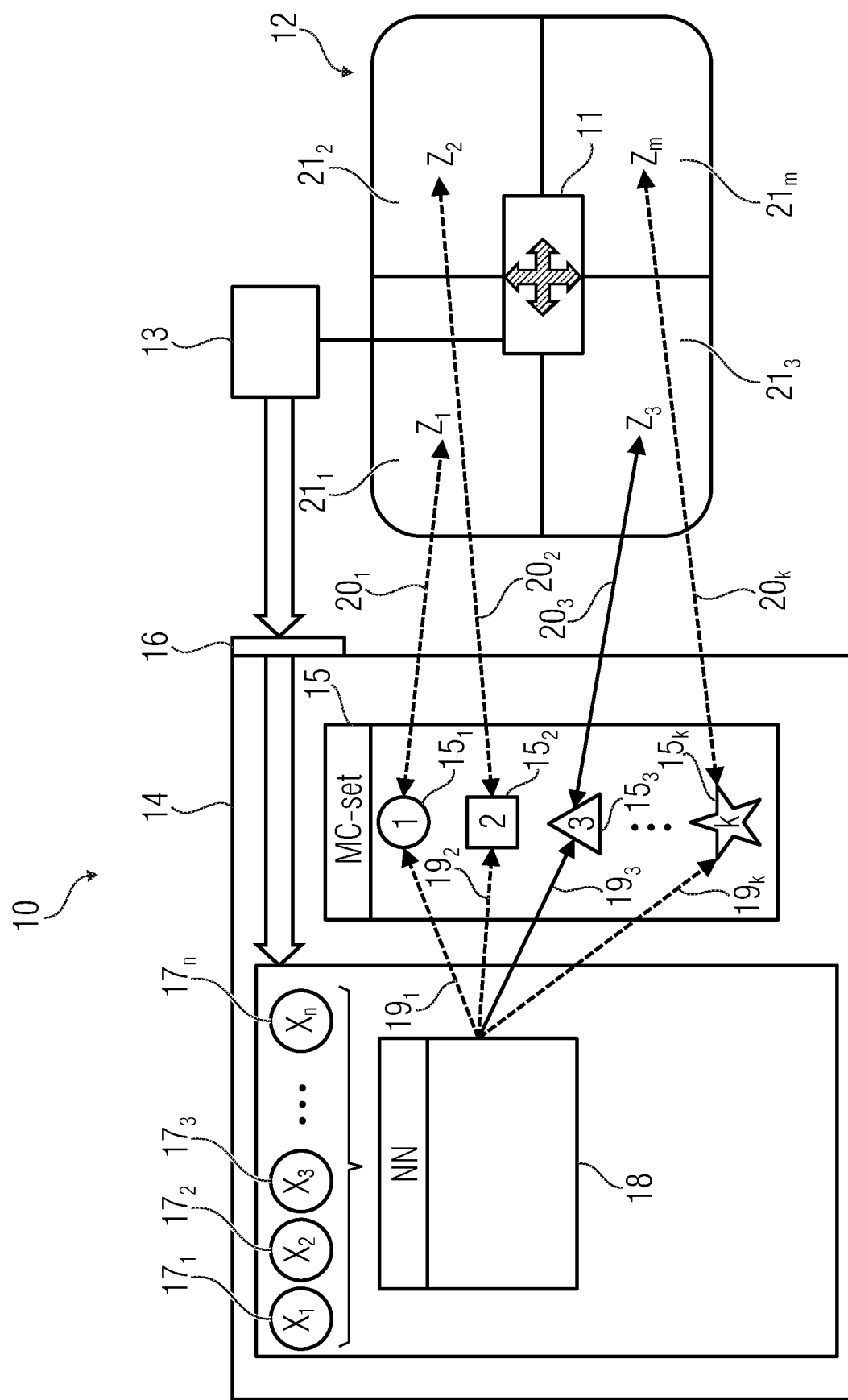
FIG. 1 shows a schematic block diagram of an example apparatus according to the present description.

Equal or equivalent elements or elements with equal or equivalent functionality are denoted in the following description by equal or equivalent reference numerals.

In the following, reference will be made to personal appliances and/or household appliances as non-limiting examples for movable treatment devices. However, these sorts of appliances are only mentioned as non-limiting examples for the sake of describing embodiments and examples of the present invention. Thus, the invention is not limited to only these mentioned kinds of appliances.

Furthermore, an order of any method steps of a method may only be described as a non-limiting example. Accordingly, any method steps as described herein may also be executed in any other order than described.

Although some aspects will be described in the context of an apparatus or device, it is clear that these aspects also represent a description of the corresponding method, where a block or device corresponds to a method step or a feature of a method step. Analogously, aspects described in the context of a method or method step also represent a description of a corresponding block or item or feature of a corresponding apparatus or device.

A first aspect of the present invention is concerned with an apparatus that is configured to localize a movable treatment device, in particular to localize the movable treatment device with respect to a target surface to be treated with said treatment device.

Examples for such movable treatment devices may be, for instance, personal appliances. A personal appliance may be, for instance, a hair brush, a razor, a shaver, an epilator, a beauty device, a groomer, a toothbrush (an electric or a manual toothbrush), or the like. In these examples, the surface to be treated may be a body or at least a certain portion or zone of said body.

Other examples of movable treatment devices may be, for instance, concerned with household appliances, such as a broom, a mop, a scrubbing brush or the like. In these examples, the surface to be treated may be a floor or wall or ceiling or at least a certain portion or zone of said floor, wall, or ceiling.

FIG. 1 shows an apparatus 10 according to an embodiment of the present invention. Furthermore, a movable treatment device 11 is depicted. The movable treatment device 11 and the apparatus 10 together form a system. The movable treatment device 11 may comprise at least one inertial sensor 13. Examples of inertial sensors 13 are motion sensors (accelerometers, which provide linear acceleration), rotation rate sensors (gyroscopes, which provide angular velocity), and orientation sensors (magnetometers) so that the position, orientation, velocity, and acceleration of the movable treatment device 11 can directly and indirectly be determined. Without being meant to be limiting, the inertial sensor may be a 3-axis inertial sensor, a 6-axis inertial sensor, or a 9-axis inertial sensor. The inertial sensors may in particular be realized as MEMS sensors. Furthermore, the movable treatment device 11 may be configured to treat a target surface 12.

As can be seen, the movable treatment device 11 may be used at a certain position or location relative to a target surface 12, for example in, at, on or next to the target surface 12. The target surface 12 itself may be divided into one or more zones $21_1, 21_2, 21_3, \ldots, 21_m$. One of the zones $21_1, 21_2, 21_3, \ldots, 21_m$ may relate to a location of the movable treatment device 11 outside of the target surface as will be explained in more detail further below. The movable treatment device 11 may be moved relative to the target surface 12. It is the basic concept behind the apparatus and system described herein that the motions of the movable treatment device 11 depend on the zone in which the movable treatment device is used and that thus the zone in which the movable treatment device 11 is used can be identified by classifying the motion, which motion is represented at least by inertial sensor data that may be extended by further sensor data, e.g. pressure sensor data.

The inventive apparatus 10, as depicted in FIG. 1, is configured to perform a localization of the movable treatment device 11 relative to the target surface 12.

In simple words, the basic concept of the present description is to use a neural network (NN) such as a recurrent neural network (RNN), in particular a Gated Recurrent Unit (GRU) RNN, an LSTM RNN (short LSTM) or a deep GRU RNN/LSTM or even a deep bi-directional GRU RNN/LSTM, to classify a temporal sequence of input vectors (based on the data from at least the at least one inertial sensor) with respect to learned motion classes, where elements of an output vector of the NN represents probabilities for each of the motion classes and then to map the sequence of output vectors of the NN to one zone of a plurality of zones relating to the use of the movable treatment device and to output this zone. Instead of mapping the sequence of output vectors to a zone, the output vectors may be mapped to a more general output, e.g. an output such as a "good" motion vs. a "bad" motion or a "correct" motion vs. an "incorrect" motion or a "first user" motion vs. a "second user" motion etc., which means that the classification happens with respect to motion classes that represent these good or bad etc. motions. This will be explained in more detail below.

The apparatus 10 may comprise a motion pattern classification device 14. The motion pattern classification device 14 may be configured to discriminate between two or more motion classes $15_1, 15_2, 15_3, \ldots, 15_k$ that are contained in a set 15 of motion classes of the movable treatment device 11. In other words, the movable treatment device 11 may be moved, e.g. by a user using said movable treatment device 11, in different linear and/or rotational directions. Accordingly, each motion of the movable treatment device 11 may represent a respective or individual motion pattern.

The motion pattern classification device 14 may comprise a set 15 of different motion classes. The set 15 of motion classes may comprise two or more motion classes $15_1, 15_2, 15_3, \ldots, 15_k$. The motion pattern classification device 14 may be configured to discriminate between these two or more motion classes $15_1, 15_2, 15_3, \ldots, 15_k$. That is, the motion pattern classification device 14 may be configured to distinguish a first motion class $15_1$ from a second motion class $15_2$. Where here it is said that the motion pattern classification device is configured to discriminate between motion classes, it is meant that the motion pattern classification device was trained to classify the input motion pattern with respect to the at least two motion classes.

The movement of the movable treatment device 11 may be detected by means of the at least one inertial sensor 13 that the movable treatment device 11 comprises. The inertial sensor 13 is a sensor based on inertia and may comprise at least one of an accelerometer, a gyroscope and a magnetometer. The inertial sensor 13 may provide sensor data representing at least one of a linear velocity, an angular velocity, a linear acceleration, an angular acceleration and a g-force. The inertial sensor 13 may be part of an inertial measurement unit comprising one or more inertial sensors.

The apparatus 10 may comprise an interface 16 for receiving at least one inertial sensor data $17_1$, $17_2$, $17_3$, ..., $17_n$ from the inertial sensor 13 and for providing the at least one inertial sensor data $17_1$, $17_2$, $17_3$, ..., $17_n$ to the motion pattern classification device 14. The at least one inertial sensor data $17_1$, $17_2$, $17_3$, ..., $17_n$ represents a movement of the movable treatment device 11. In other words, when the movable treatment device 11 moves, the inertial sensor 13 senses this motion and creates at least one inertial sensor data $17_1$, $17_2$, $17_3$, ..., $17_n$. Accordingly, the at least one inertial sensor data $17_1$, $17_2$, $17_3$, ..., $17_n$ represents the respective motion of the moved treatment device 11. Inertial sensor data $17_1$, $17_2$, $17_3$, ..., $17_n$ may be sampled from the inertial sensor 13 in temporal succession. While it shall not be excluded that a single sample of inertial sensor data relating to one given time instant is inputted into the motion pattern classification device to classify the motion pattern with respect to the at least two motion classes $15_1$, $15_2$, $15_3$, ..., $15_k$, the interface may in particular input a temporal sequence of inertial sensor data into the motion pattern classification device 13 so that the temporal relationship of the inertial sensor data can be utilized in the classification process.

According to the present disclosure, the motion pattern classification device 14 may comprise a neural network 18. The neural network 18 may be a recurrent neural network or a deep neural network. The neural network 18 may be configured to receive the at least one inertial sensor data $17_1$, $17_2$, $17_3$, ..., $17_n$ and to classify the at least one inertial sensor data $17_1$, $17_2$, $17_3$, ..., $17_n$ with respect to at least one of the motion classes $15_1$, $15_2$, $15_3$, ..., $15_k$ contained in the set 15 of motion classes (the number n of inertial sensor data is independent from the number k of motion classes, i.e. 25 input vectors may be provided and 12 motion classes are used). This classification is schematically indicated in FIG. 1 by means of the dashed and solid arrows $19_1$, $19_2$, $19_3$, ..., $19_k$. The arrow $19_3$ that is drawn in solid lines may exemplarily indicate that the neural network 18 successfully classified the at least one inertial sensor data $17_1$, $17_2$, $17_3$, ..., $17_n$ to the third motion class $15_3$. It is understood that the output of the NN typically has the same sequence length as the input, i.e. in case ten input vectors are provided as input sequence then ten output vectors are provided as output sequence (i.e. the RNN unit always produces an output vector per time instant) and in case only one input vector is provided then also only one output vector is provided. Typically, each output vector of the NN comprises k elements that relate to the k motion classes and each element of the output vector provides a probability that the input motion pattern of the same time instant relates to the respective corresponding motion class.

The different motion classes $15_1$, $15_2$, $15_3$, ..., $15_k$ that are contained in the set 15 are exemplarily symbolized by different geometrical shapes (circle, rectangle, triangle, star) merely for illustration purposes.

According to the basic principle, the motion classes $15_1$, $15_2$, $15_3$, ..., $15_k$ are each associated with one or more different zones $21_1$, $21_2$, $21_3$, ..., $21_m$ of the target surface 12. This is indicated by means of the dashed and solid arrows $20_1$, $20_2$, $20_3$, ..., $20_k$. As can be seen, the first motion class $15_1$ may be associated with a first zone $21_1$ of the target surface 12, as is indicated by the dashed arrow $20_1$. The second motion class $15_2$ may be associated with a second zone $21_2$ of the target surface 12, as is indicated by the dashed arrow $20_2$. The third motion class $15_3$ may be associated with a third zone $21_3$ of the target surface 12, as is indicated by the arrow $20_3$ that is drawn in solid lines. The $k^{th}$ motion class $15_k$ may be associated with an $m^{th}$ zone $21_m$ of the target surface 12, as is indicated by the dashed arrow $20_k$. While this is generally known to the person skilled in the art of neural networks, it is here stated that the neural network is first trained with labelled input motion patterns, i.e. motion patterns that are known to relate to a certain motion class, so that the neural network used in the apparatus 10 is of course a trained neural network that can classify a new input motion pattern with respect to the motion classes $15_1$, $15_2$, $15_3$, ..., $15_k$ comprised in the set of (trained) motion classes 15 with a certain prediction probability.

The arrow $20_3$ that is drawn in solid lines may exemplarily indicate that the third motion class $15_3$, to which the at least one inertial sensor data $17_1$, $17_2$, $17_3$, $17_n$ was successfully classified by the neural network 18, is associated with the third zone $21_3$ of the target surface 12. The differentiation made herein between motion classes $15_1$, $15_2$, $15_3$, ..., $15_n$ and zones $21_1$, $21_2$, $21_3$, ..., $21_m$ of the target surface 12 is to some extent artificial if motion classes and zones are associated to each other by a bijective (i.e. a one-to-one and onto) function, but this differentiation is made as it allows that that the neural network was trained to classify inputs (i.e. motion patterns) with respect to a first number of motion classes $15_1$, $15_2$, $15_3$, ..., $15_k$, let's say k=20, and that the output of the neural network is mapped onto a lower (or higher) number of zones $21_1$, $21_2$, $21_3$, ..., $21_m$, let's say m=6. As will be explained further below, one or several of the motion classes may be associated with two or more zones (e.g. motion class 5 may be associated with zones 3 and 4). While this should be clear from the above, it is here repeated that the NN does not classify the input motion pattern with respect to the zones but only with respect to the motion classes and that the step of identifying the zone is an added step that may involve various additional computational steps (as will be explained in more detail further below) and in particular, the number m of zones may be lower (or higher, which means: different) than the number k of motion classes. Further in particular, the apparatus may output a zone only per input vector sequence, e.g. the apparatus may output zone 6 as the zone in which the apparatus was used during the time period relating to the current input vector sequence. A maximum criterium or majority criterium may be used to map the output vector sequence onto the single zone output, as will be explained further below.

Accordingly, the classification of the at least one inertial sensor data $17_1$, $17_2$, $17_3$, ..., $17_n$ with respect to the at least one motion class $15_1$, $15_2$, $15_3$, ..., $15_k$ indicates an estimation of the location of the movable treatment device 11 with respect to the one or more zones $21_1$, $21_2$, $21_3$, ..., $21_m$ of the target surface 12. In the present example, the classification of the at least one inertial sensor data $17_1$, $17_2$, $17_3$, $17_n$ with the third motion class $15_3$ indicates an estimation of the location of the movable treatment device 11 with respect to the third zone $21_3$ of the target surface 12. As will be explained in more detail below, the output vector $y_t$ of a neural unit of the neural network described herein typically provides probability values that the input motion pattern relates to each of the motion classes.

In other words, the neural network 18 successfully classified the received at least one inertial sensor data $17_1$, $17_2$, $17_3$, $17_n$ to the third motion class $15_3$ (the probability value of the output vector $y_t$ for motion class $15_3$ is the highest probability value). Since, according to this example, the third motion class $15_3$ is associated with the third zone $21_3$, the apparatus 10 retrieves the information that the movable treatment device 11 may be located at the third zone $21_3$, or that the movable treatment device 11 at least was located at the third zone $21_3$ at the time when the at least one inertial sensor data $17_1$, $17_2$, $17_3$, ..., $17_n$ was created.

Thus, the apparatus 10 may be configured to localize the movable treatment device 11 relative to the target surface 12 simply by means of the executed motion, or motion pattern, of the movable treatment device 11.

According to an embodiment, the movable treatment device 11 may be a personal appliance and the target surface 12 may be a body portion to be treated by the movable treatment device 11.

For example, the movable treatment device 11 is a razor or a groomer for shaving or grooming a body portion of a user's body. The user's body may be the target surface 12 in this case. The user's body 12 may be separated into different zones, for instance, a left cheek zone, a right cheek zone, a chin zone and so on. By executing a certain motion pattern with the razor 11 the apparatus 10 can localize the razor 11 relative to the user's body using the trained neural network.

As a further example, the movable treatment device 11 is a household appliance and the target surface 12 may be a surface of a floor, a wall, a furniture or the like. For example, the movable treatment device 11 may be a vacuum cleaner and the target surface 12 may be the floor of a room. The room 12 may be separated into different zones, for instance, a left top corner of the room, a right bottom corner of the room, a center of the room, underneath a bed located inside the room, and so on. By executing a certain motion pattern with the vacuum cleaner 11 the apparatus 10 may localize the vacuum cleaner 11 relative to the floor of the room. For instance, if the vacuum cleaner 11 executes a motion pattern that is merely directed forwards and backwards with the lance of the vacuum cleaner 11 being lowered near to the ground, the apparatus 10 may localize the vacuum cleaner 11 as being located in the "underneath the bed" zone, for example. Accordingly, the apparatus 10 may localize the vacuum cleaner 11 inside the room simply by its executed motion pattern.

According to a further embodiment, the movable treatment device 11 is an oral care device and the target surface 12 may be an oral cavity, wherein the oral cavity 12 is separated into different zones $21_1$, $21_2$, $21_3$, ..., $21_m$, wherein the classification of the at least one inertial sensor data $17_1$, $17_2$, $17_3$, $17_n$ with respect to the at least one motion class $15_1$, $15_2$, $15_3$, ..., $15_k$ indicates an estimation of the location of the oral care device 11 with respect to the one or more oral cavity zones $21_1$, $21_2$, $21_3$, ..., $21_m$ of the oral cavity 12. The oral cavity prominently comprises the dentition, where the dentition may be separated into different dental zones (as will be explained in more detail further below), but the oral cavity also comprises a tongue (in particular, the tongue may be separated into different tongue sections) and gums and cheek sections, which areas may be zones as well and motion classes may be trained so that the neural network can classify input motion patterns onto a motion class that relates to the tongue etc.

The oral care device may be a toothbrush, in particular an electric toothbrush. The oral care device may also be at least one of a dental floss, a plaque removing device, an ultrasound device and a waterjet device.

According to this example, by executing a certain motion pattern with the oral care device 11 the apparatus 10 may localize the oral care device 11 relative to the oral cavity, e.g. relative to the dentition. For instance, if the oral care device 11 executes a motion pattern that is merely directed upwards and downwards with the oral care device 11 being tilted to the left, the apparatus 10 may localize the oral care device 11 as being located in a left upper dental zone of the upper jaw, for example, due to the classification of the motion onto the learned motion classes and by further mapping the identified motion class onto a zone either for each time instant or for the whole time sequence of input data. Accordingly, the apparatus 10 may localize the oral care device 11 relative to the user's dentition simply by its executed motion pattern. The input motion patterns described herein by means of example shall only illustrate the basic concept. As a matter of fact, the motion patterns relating to a certain zone (e.g. to the upper front teeth) heavily depend on the individual and the brushing habits of the individual, e.g. the individual may be a right-handed or a left-handed person, the individual may use scrubbing etc. It is obvious that the training phase of the neural network may include as many different individuals or user types and circumstances affecting the brushing habits so that the prediction quality of the neural network may be high for all types of input motion patterns.

According to an embodiment, the dentition may be separated into nine dental zones, wherein a first dental zone corresponds to the left buccal side of the upper and lower jaw of the dentition, a second dental zone corresponds to the occlusal side of the left and right side of the upper jaw of the dentition, a third zone corresponds to the occlusal side of the left and right side of the lower jaw of the dentition, a fourth dental zone corresponds to the left lingual side of the upper and lower jaw of the dentition, a fifth dental zone corresponds to the right buccal side of the upper and lower jaw of the dentition, a sixth dental zone corresponds to the right lingual side of the upper and lower jaw of the dentition, a seventh dental zone corresponds to the labial side of the upper and lower jaw of the dentition, an eighth dental zone corresponds to the palatal side of the upper jaw of the dentition, a ninth dental zone corresponds to the oral side of the front lower jaw of the dentition.

According to a further embodiment, at least one motion class $15_{NB}$ that may be additionally contained in the set 15 of motion classes may be associated with a zone $21_{NB}$ outside the target surface 12, or not related to the target surface 12, wherein the mapping of the at least one inertial sensor data $17_1$, $17_2$, $17_3$, ..., $17_n$ with the at least one motion class $15_{NB}$ indicates that the movable treatment device 11 is located in said zone $21_{NB}$ that is outside the target surface 12, or not related to the target surface 12. Motion class $15_{NB}$ may relate to input motion patterns where the user moves the movable treatment device 11 towards the target surface (e.g. an oral care device was placed on the bathroom sink and is moved towards the oral cavity) or where the user transitions the movable treatment device 11 from one zone to another zone (e.g. the user may move an oral care device from the upper left molars towards the lower right molars).

In other words, the zone $21_{NB}$ outside the target surface 12 may be a zone that is not directly related to the target surface 12. For example, if the movable treatment device 11 may be a toothbrush, then said zone $21_{NB}$ outside the target surface 12 may be a zone outside the dentition. Accordingly, this zone $21_{NB}$ may indicate that the user is not brushing his teeth. Thus, this zone may also be referred to as a zone 'Not Brushing', abbreviated by 'NB'. This zone $21_{NB}$ may be the at least one zone of the target surface 12, or this zone $21_{NB}$ may be an additional zone in addition to the one or more zones $21_1, 21_2, 21_3, \ldots, 21_m$ of the target surface. However, this particular zone $21_{NB}$ outside the target surface 12 is not limited to the above-described example of teeth brushing. It shall not be excluded that the motion pattern classification device comprises a set of motion classes with one or more of the motion classes each being associated with one or more zones outside of the target surface, e.g. at least one motion class may be associated with a zone outside of the target surface (e.g. when the apparatus is moved towards or away from the target surface) and/or at least one motion class may be associated with a transition between zones of the target surface (e.g. when the apparatus is moved from zone 3 to zone 4).

Figure 2:
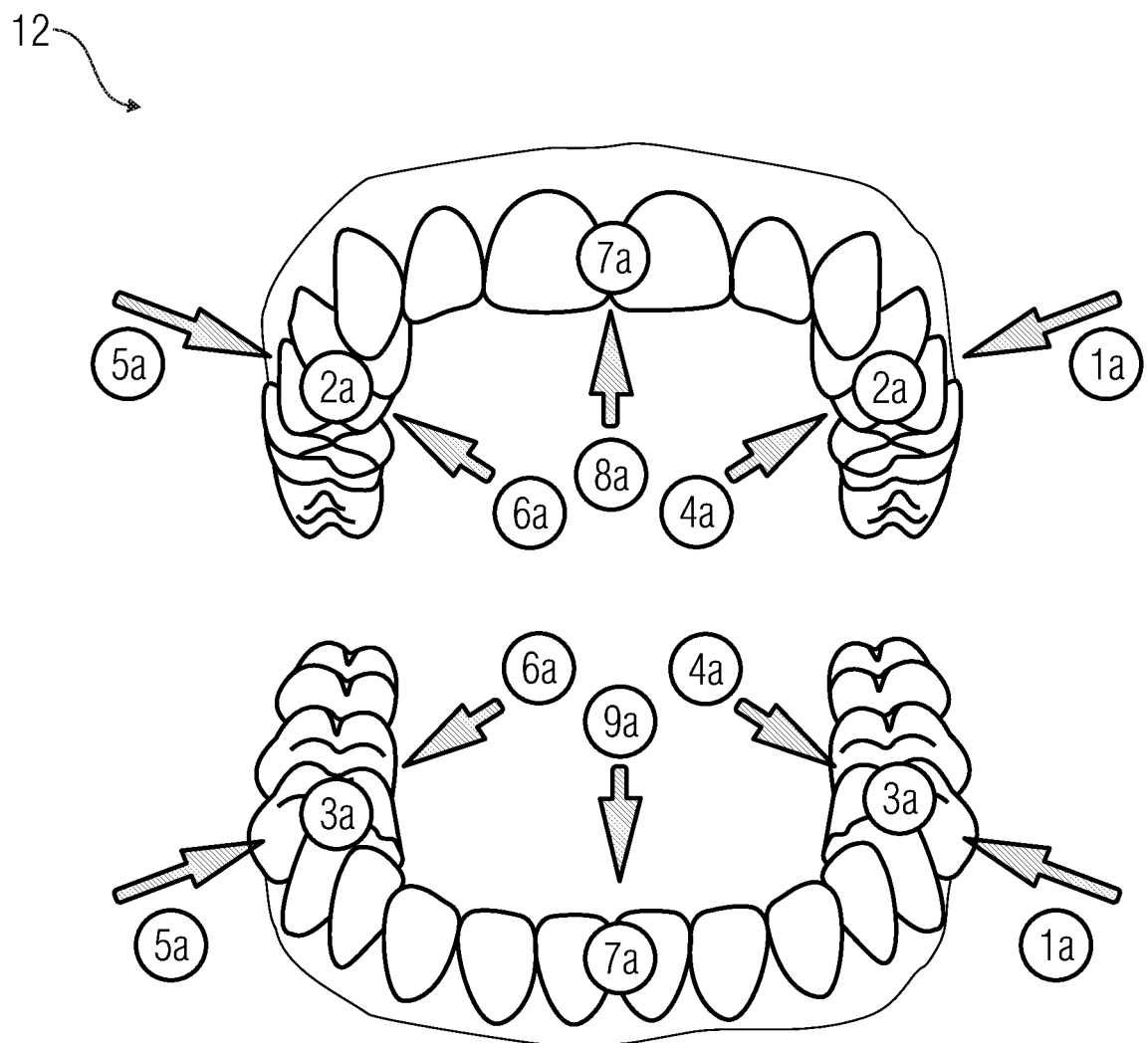
FIG. 2 shows an example of a target surface to be treated with the movable treatment device.

FIG. 2 shows a dentition 12 for illustrating the above-described example. The dentition 12 may be the target surface or may be a part of the target surface, which may include, e.g., also the tongue. The dentition 12 may be separated into nine dental zones 1a to 9a. Optionally, a tenth zone NB may exist. This tenth zone NB is a zone outside the dentition 12. Thus, this tenth zone NB is not explicitly illustrated in FIG. 2. Since this tenth zone NB is not related to one of the dental zones of the dentition 12, and therefore not concerned with brushing the teeth of the dentition 12, this tenth zone NB may also be referred to as a 'Not Brushing' zone.

As can be seen in FIG. 2, a first dental zone 1a may correspond to the left buccal side of the upper and lower jaw of the dentition 12. A second dental zone 2a may correspond to the occlusal side of the left and right side of the upper jaw of the dentition 12. A third zone 3a may correspond to the occlusal side of the left and right side of the lower jaw of the dentition 12. A fourth dental zone 4a may correspond to the left lingual side of the upper and lower jaw of the dentition 12. A fifth dental zone 5a may correspond to the right buccal side of the upper and lower jaw of the dentition 12. A sixth dental zone 6a may correspond to the right lingual side of the upper and lower jaw of the dentition 12. A seventh dental zone 7a may correspond to the labial side of the upper and lower jaw of the dentition 12. An eighth dental zone 8a may correspond to the palatal side of the upper jaw of the dentition 12. A ninth dental zone 9a may correspond to the oral side of the front lower jaw of the dentition 12. A further zone may correspond to the tongue.

Figure 3:
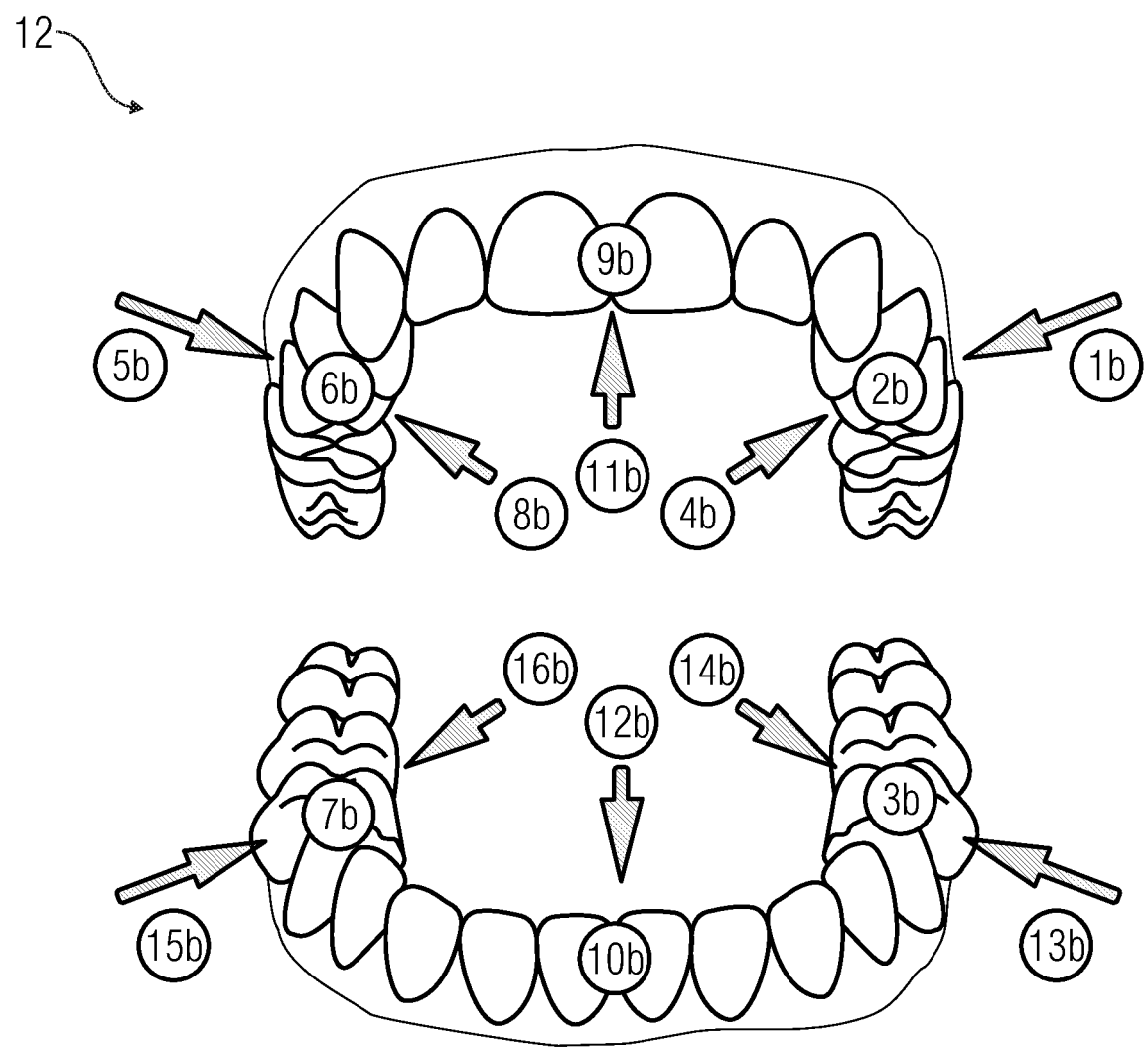
FIG. 3 shows a further example of a target surface to be treated with the movable treatment device.

FIG. 3 shows a dentition 12 for illustrating a further example. The dentition 12 may be the target surface. The dentition 12 may be separated into sixteen dental zones 1b to 16b. Optionally, a seventeenth zone NB may exist. This seventeenth zone NB is a zone outside the dentition 12. Thus, this seventeenth zone NB is not explicitly illustrated in FIG. 3. Since this seventeenth zone NB is not related to one of the dental zones of the dentition 12, and therefore not concerned with brushing the teeth of the dentition 12, this seventeenth zone NB may also be referred to as a 'Not Brushing' zone.

As can be seen in FIG. 3, a first dental zone 1b may correspond to the left buccal side of the upper jaw of the dentition 12. A second dental zone 2b may correspond to the occlusal side of the left side of the upper jaw of the dentition 12. A third dental zone 3b may correspond to the occlusal side of the left side of the lower jaw of the dentition 12. A fourth dental zone 4b may correspond to the left lingual side of the upper and lower jaw of the dentition 12. A fifth dental zone 5b may correspond to the right buccal side of the upper and lower jaw of the dentition 12. A sixth dental zone 6b may correspond to the occlusal side of the right side of the upper jaw of the dentition 12. A seventh dental zone 7b may correspond to the occlusal side of the right side of the lower jaw of the dentition 12. An eighth dental zone 8b may correspond to the palatal side of the upper jaw of the dentition 12. A ninth dental zone 9b may correspond to labial side of the upper jaw of the dentition 12. A tenth dental zone 10b may correspond to the labial side of the lower jaw of the dentition 12. An eleventh dental zone 11b may correspond to the palatal side of the upper jaw of the dentition 12. A twelfth dental zone 12b may correspond to the oral side of the front lower jaw of the dentition 12. A thirteenth dental zone 13b may correspond to the left buccal side of the lower jaw of the dentition 12. A fourteenth dental zone 14b may correspond to the left lingual side of the lower jaw of the dentition 12. A fifteenth dental zone 15b may correspond to the right buccal side of the lower jaw of the dentition 12. A sixteenth dental zone 16b may correspond to the right lingual side of the lower jaw of the dentition 12.

In this example, sixteen motion classes may be trained (or seventeen motion classes, including the non-brushing motion class) and a bijective function may be used to associate the motion classes and the zones with each other. With reference to the oral care example, further motion classes may be trained. For example, it is known that users tend to brush the outer sides of the left molars (i.e. the buccal surfaces of the left molars) together instead of individually brushing the buccal surfaces of the upper left molars and the buccal surfaces of the lower left molars. Thus, the neural network may be trained to classify the input motion pattern with respect to a further motion class that relates to this combined brushing of the buccal surfaces of the left molars. This motion class is then associated with two of the previously mentioned zones, namely the first dental zone 1b and the thirteenth dental zone 13b. Consequently, further trained motion classes may relate to the outer surfaces of the front teeth and to the buccal surfaces of the right molars. In such an example, twenty motion classes are used and are associated with seventeen zones.

FIGS. 2 and 3 have only been described as non-limiting examples. The target surface 12 may also comprise more or less than the described nine or sixteen dental zones. Furthermore, the tenth/seventeenth dental zone NB outside the target surface 12 is optional. The exact distribution of the one or more dental zones of the dentition 12 may vary from the examples described above.

The neural network 18 may be a Recurrent Neural Network (RNN). For example, the neural network may be a Long Short-Term Memory (LSTM) network or a Gated Recurrent Unit (GRU) network. The RNN may be a bi-directional recurrent neural network. That means that a sequence of input vectors is fed into a first recurrent neural network that computes the output from left to right (e.g. from past to future) and into a separate second recurrent neural network that computes the output from right to left (e.g. from future to past). In this manner, the RNN can make use of past and of future features in the input sequence. The forward and backward hidden vectors of the two separate RNNs are then together fed into the output layer to generate the output vector sequence.

Alternatively, the apparatus 10 may make use of two different neural networks. With reference to the dentition example, a first neural network may classify the input motion pattern into motion classes for left molars, right molars, and front teeth and a second neural network may classify the input motion pattern into motion classes for the upper jaw and the lower jaw. One may call this a segmentation into orthogonal motion classes. The outputs of the first and second neural networks may then be combined to output one of six zones of the dentition, namely the upper left molars, the upper right molars, the lower left molars, the lower right molars, the upper front teeth, or the lower front teeth. This represents at least an alternative over directly using a single neural network that outputs probability values for the mentioned six motion classes. The use of two neural networks may be extended by further neural networks, e.g. a third neural network may classify the input motion patterns into motion classes for buccal and lingual (and occlusal) surfaces of the teeth.

As was already mentioned, the interface may be arranged to provide a sequence of inertial sensor data to the motion pattern classification device, where here sequence relates to a temporal sequence. It was found that for toothbrushing, a sequence length in the range of 20 to 30 inertial sensor data represents a sensible sequence length and that the time period in which these inertial sensor data were sampled may be in the range of between 0.5 seconds and 5 seconds, in particular may be about 1 second.

RNNs may suffer from the so-called vanishing gradient problem, wherein gradients vanish quickly with more number of layers. Vanishing gradients may lead to rather slow training rates. Thus, LSTM networks and/or GRU networks may be used to avoid the vanishing gradient problem.

An LSTM network is an artificial neural network containing LSTM modules or units in addition to regular network units (e.g. such as a fully connected output layer). Here, the terms LSTM module or LSTM unit or LSTM cell or LSTM block shall all mean the same, namely a complete LSTM unit as exemplary depicted in FIG. 6a. An LSTM module contains gates that determine when the input is significant enough for the LSTM unit to remember, when it should continue to be remembered or when it should forget the value.

Figure 4:
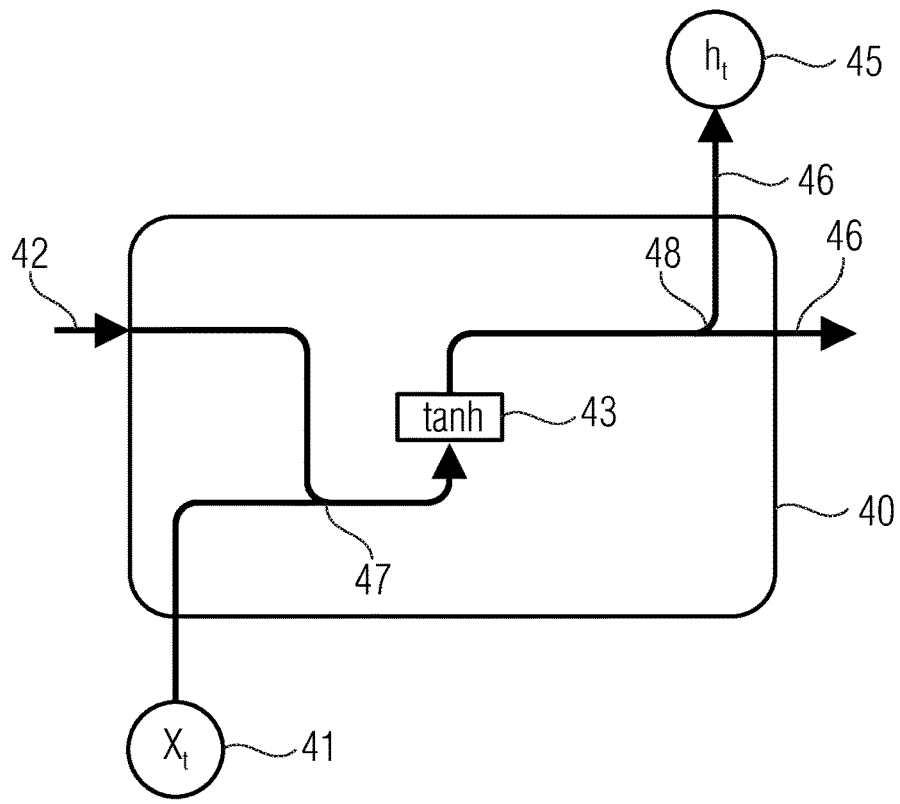
FIG. 4 shows a schematic block diagram of a repeating module (or unit or block or cell) that may be used in a recurrent neural network.

FIG. 4 shows an example of an RNN module 40 in a simple form. The module 40 (which may also be called a neural unit) may be fed with an input 41 at a certain time instant t. The input 41 may be a single value or a vector comprising two or more values. The input 41 at the certain time instant t may also be symbolized with $X_t$. The value or values of the input 41 may be raw data from an inertial sensor. In case a six-axis inertial sensor is used (e.g. a three-axis accelerometer and a three-axis gyroscope), the input 41 may have six values, i.e. the vector $X_t$ has six vector elements or in other words: $X_t \in \mathbb{R}^6$.

As was already mentioned, the movable treatment device may comprise further sensors, e.g. a pressure sensor that measures the pressure with which the movable treatment device is pushed against the treatment surface. In such an example, the pressure may be sampled in the same manner and the input 41 may then, e.g., get a seventh element, namely the pressure value so that $X_t$ where a single pressure value is assumed. The pressure (or force) sensor may instead be a multi-axis pressure (or force) sensor and the input may then have an even higher dimension. The pressure value may improve the classification quality of the neural network. The neural unit 40 may also comprise a further input 42. This further input 42 may be provided from a neural unit (not depicted here) at a previous time instant t−1. The computation direction of the recurrent neural network is not bound to run in positive time direction (i.e. from past to future). In case that a sequence of inertial sensor data is inputted into the RNN, the recurrent neural network may compute from the temporally last inertial sensor data towards the temporally first inertial sensor data (i.e. from future to past) or vice versa. As was already mentioned, the RNN may be a bi-directional RNN having one branch that computes from past to future and another branch that computes from future to past. That means that the term "previous time instant" only refers to the previous time instant with respect to the computation direction but does not necessarily mean a temporally earlier time instant.

The neural unit 40 may comprise at least one neural network layer 43, which may provide a mathematical operation. In this example, the gate 43 is a single tan h layer. It shall be understood that the neural network layers shown as boxes indicate a learned network layer.

The neural unit 40 may comprise at least one output 46. The output 46 may comprise the result of the operation of the tan h neural network layer 43 that has been fed with the input 41 and optionally the further input 42. The output 46 may lead to a hidden state 45, which will be explained later.

The neural unit 40 may optionally comprise a further output branch 46 which branches off from the above-mentioned output result of the operation of the tan h gate 43 fed with the input 41 and optionally the further input 42.

In FIG. 4, each depicted line may carry an entire vector, from the output of one node to the inputs of others. Lines merging, for instance at 47, denote concatenation, while a line forking, for instance at 48, denote its content being copied and the copies going to different locations. This holds true also for the other neural network units that will be described in the following with reference to the following Figures.

While this is generally known by a person skilled in the art of neural networks, the input vector $X_t$, which may comprise six values, may be mapped onto a vector having a much higher dimension in an input layer of the module 40, e.g. the vectors used in the NN module 40 may be vectors in $\mathbb{R}^{256}$, where it shall here be understood that this is just a non-limiting example. Typical values for the dimensions of vectors in a neural network may be 128, 256, 512, or 1024, but other values may be chosen as well. The input weight matrix for performing this mapping is thus a $\mathbb{R}^6 \times \mathbb{R}^{256}$ matrix. A bias vector may be used as is known in the art, which bias vector again may then be vector in $\mathbb{R}^{256}$. The output vector $h_t$ of the module 40 is also a vector in $\mathbb{R}^{256}$. Assuming that the RNN has only a single repeating chain of modules as shown in FIG. 4, an output layer may then map each of the output vectors $h_t$ onto an output vector having the dimension in accordance with the number of motion classes, e.g. $\mathbb{R}^{20}$ in case of 20 motion classes. The output weight matrix is then a $\mathbb{R}^{256} \times \mathbb{R}^{20}$ matrix. As was mentioned before, the weights and biases are determined in the training phase.

Figure 5:
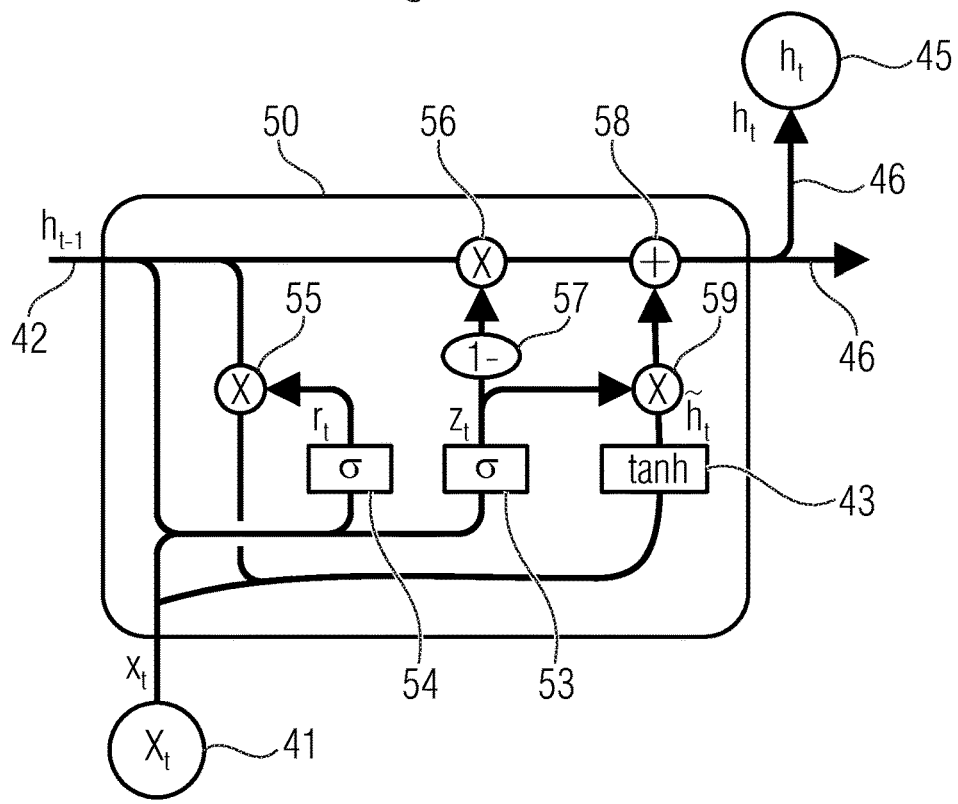
FIG. 5 shows a schematic block diagram of a repeating gated recurrent unit (GRU) module that may be used in a recurrent neural network.

FIG. 5 shows an example of a GRU module 50 that can be used in a RNN. In addition to the above-described simple RNN neural unit 40, the GRU neural unit 50 may comprise two further neural network layers, namely a first sigmoid layer 53 and a second sigmoid layer 54. Furthermore, the GRU neural unit 50 may comprise pointwise operations 55, 56, 57, 58, 59, like vector addition 58, for example.

Figure 6A:
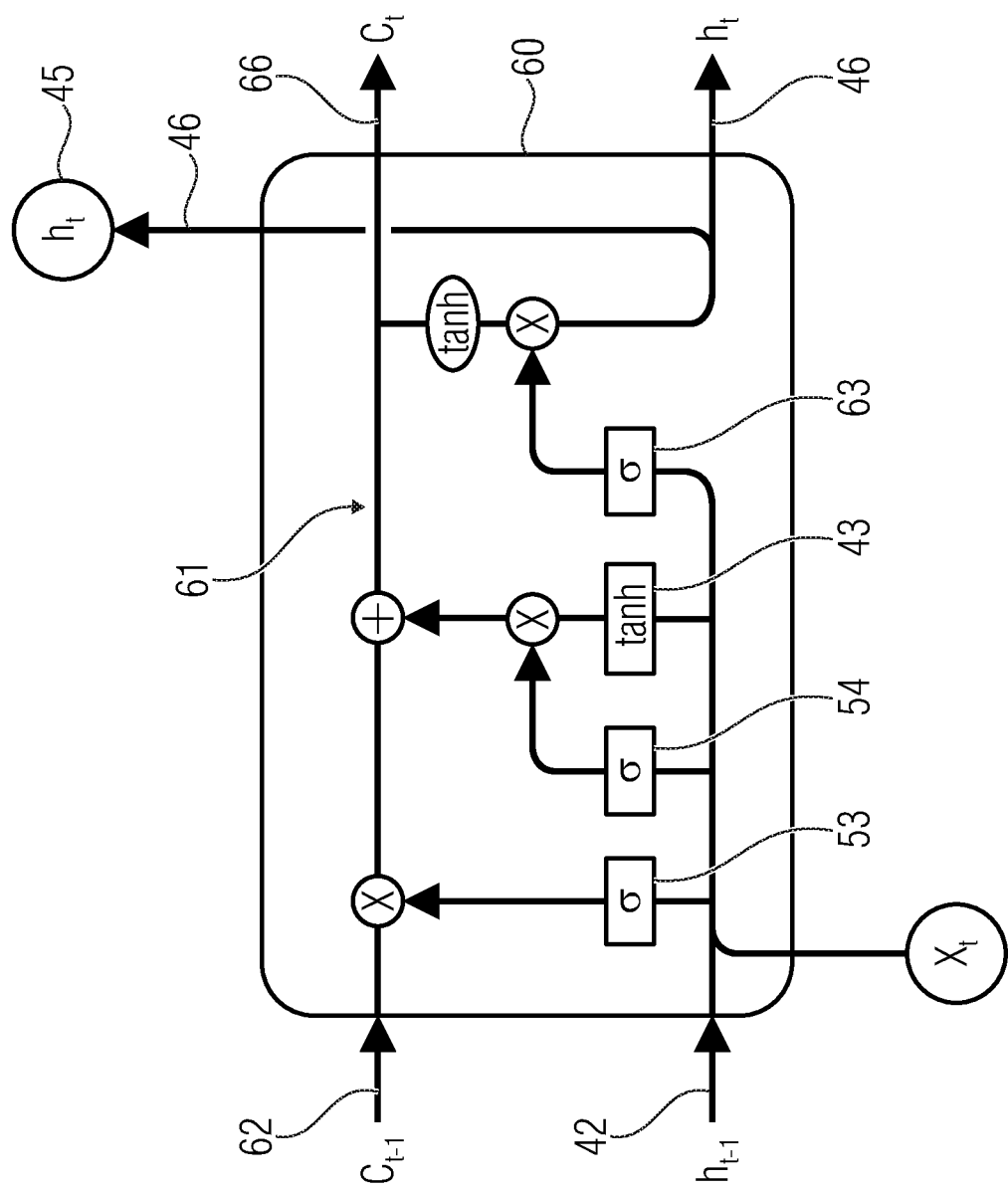
FIG. 6A shows a schematic block diagram of a repeating LSTM module (or unit) that may be used in a recurrent neural network.

FIG. 6a shows an example of a repeating module 60 commonly known as a LSTM module that may be exploited in the neural network 18 in the apparatus 10 according to the invention. In addition to the above-described neural units 40, 50, the LSTM unit 60 may comprise a cell state, which is the horizontal line 61 running through the top of the neural unit 60. The neural unit 60 may receive a cell state input 62 and may create a cell state output 66.

The neural unit 60 may comprise three gates (or gate layers), namely an input gate 54, an output gate 63, and a forget gate 53. Each of these gates 53, 54, 63 can be thought of as a "standard" neuron in a feed-forward (or multi-layer) neural network: that is, they compute an activation (using an activation function) of a weighted sum. Information may be removed or added to the cell state (horizontal line 61) by means of these gates 53, 54, 63. The input gate 54 is combined with a tan h layer 43 that creates a candidate state that together with the input gate determines the update of the cell state. See also the set of equations shown and discussed further below describing the flow within an LSTM unit.

It shall be understood that the neural units 50 and 60 are just shown and discussed as example neural units. Other neural units may make use of peephole connections and/or connected forget and input gate layers. Long-term dependencies may also be approached by, e.g., Clockwork RNNs or other multiscale RNNs.

Figure 6B:
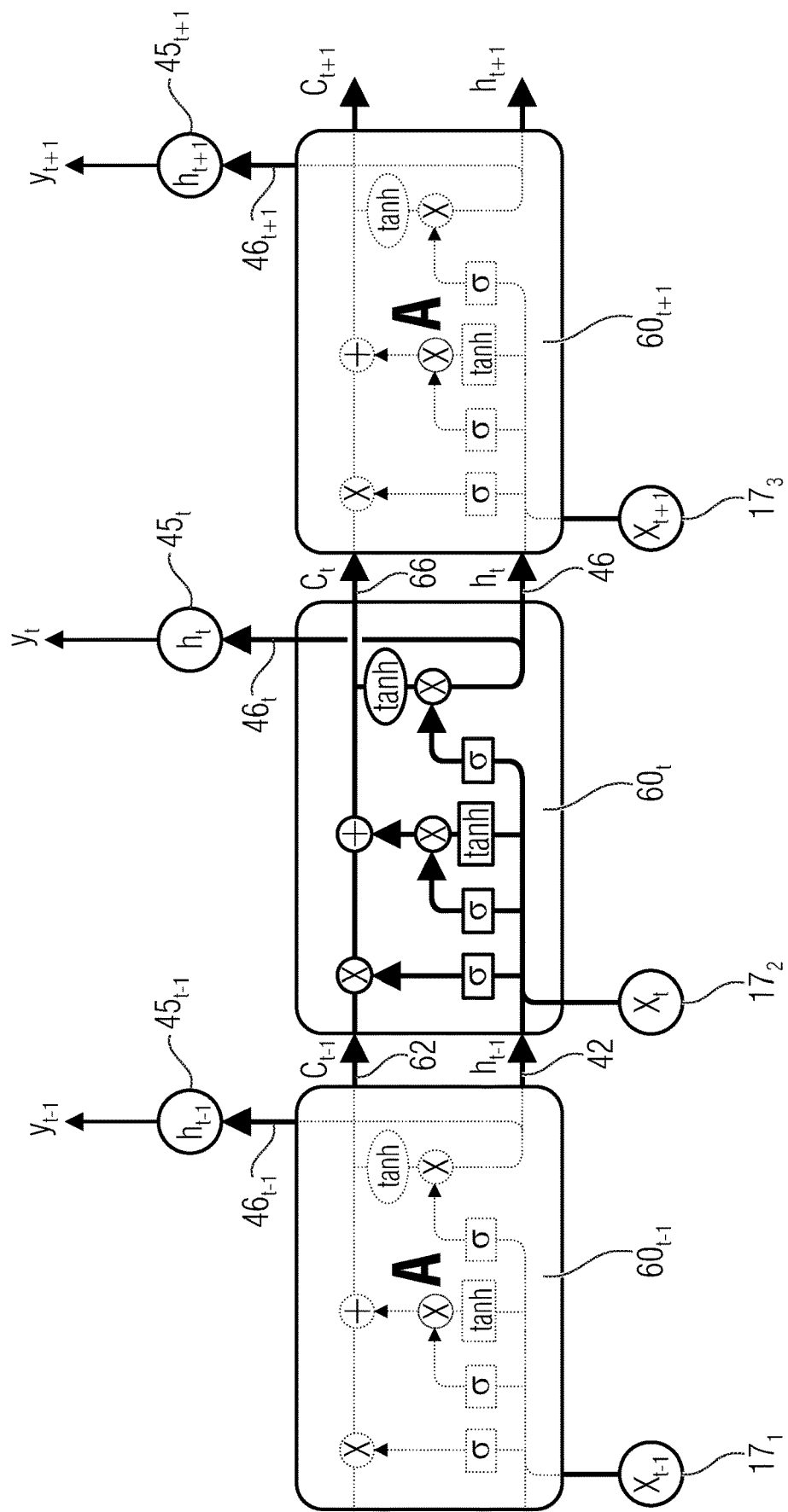
FIG. 6B shows a schematic block diagram of an unrolled LSTM module-based recurrent neural network with one layer of LSTM modules at different time instances.

FIG. 6b shows an example of an unrolled RNN comprising a LSTM module in which previous and subsequent states (with respect to the time instant t) of the neural unit are depicted. In particular, a neural unit $60_t$ at a time instant t is depicted. Furthermore, a further neural unit $60_{t-1}$ at a previous time instant t−1 is depicted. Still further a further neural unit $60_{t+1}$ at a subsequent time instant t+1 is depicted. The depicted neural units $60_{t-1}$, $60_t$, $60_{t+1}$ may represent the same neural unit but at different points in time, namely at the time instant t, at a previous time instant t−1 and at a subsequent time instant t+1. FIG. 6b may be understood as a portion of the unrolled LSTM network that has as many repeating neural units as there are input vectors $X_t$ in an input sequence. As was mentioned before, a sequence length in the range of 20 to 30, e.g. about 25, may be used.

The above-described input 41, also symbolized by the letter X, may comprise the at least one sensor data $17_1$, $17_2$, $17_3$, $17_n$ from the inertial sensor 13. The input X may be time dependent, thus X=X(t). In particular, the depicted input $X_t$ may comprise a sensor data $17_2$ acquired during the considered time instant t, the depicted input $X_{t-1}$ may comprise a sensor data $17_1$ acquired during a previous time instant t−1, and the depicted input $X_{t+1}$ may comprise a sensor data $17_3$ acquired during a subsequent time instant t+1. As was explained before, the input X is fed into an input layer of the RNN.

As can further be seen in FIG. 6b, the neural units $60_{t-1}$, $60_t$, $60_{t+1}$ may, in each depicted time instant t−1, t, t+1, provide a respective output value $y_{t-1}$, $y_t$, $y_{t+1}$. The output value y(t) may be a single value (in case there would be only one single motion class) or a vector comprising a plurality of vector elements.

The output value y(t) may be calculated in a fully connected output layer of the RNN as:

$$y_t = \text{softmax}(W_{hy} \cdot h_t + b)$$

where $W_{hy}$ is the respective output weight matrix and b is the respective output bias vector. The output vector y(t) comprises probabilistic values in the range of between 0 and 1, as will be explained in more detail with respect to FIG. 7. The output vector y(t) comprises one or more vector elements, wherein each vector element provides a probability value that the input vector $X_t$, i.e. the inertial sensor data $17_1$, $17_2$, $17_3$, ..., $17_n$, relates to one of the motion classes $15_1$, $15_2$, $15_3$, ..., $15_k$. It shall be understood that the application of the softmax function is merely optional. In particular, the identification of the motion class having the highest probability in the output vector can be done without any normalization.

Furthermore, the depicted neural units $60_{t-1}$, $60_t$, $60_{t+1}$ may be arranged in the same layer, namely in a first layer. Some examples of the invention may comprise one or more further stacked layers, wherein each layer may comprise its own neural unit(s). Such examples may be described later with reference to FIG. 7 for example. However, examples and embodiments with at least a first layer will be described with further reference to FIG. 6b.

According to this embodiment, the neural network 18 may comprise a first layer of neural units $60_{t-1}$, $60_t$, $60_{t+1}$, here of LSTM units, wherein said first layer comprises a neural unit $60_t$, wherein at a first time instant t the at least one inertial sensor data $X_t$ is input into the neural unit $60_t$ of the first layer. At a subsequent second time instant t+1 a second inertial sensor data $X_{t+1}$ and at least one output $h_t$ of the neural unit $60_t$ of the previous first time instant t are input into the neural unit $60_{t+1}$ of the first layer.

Figure 7:
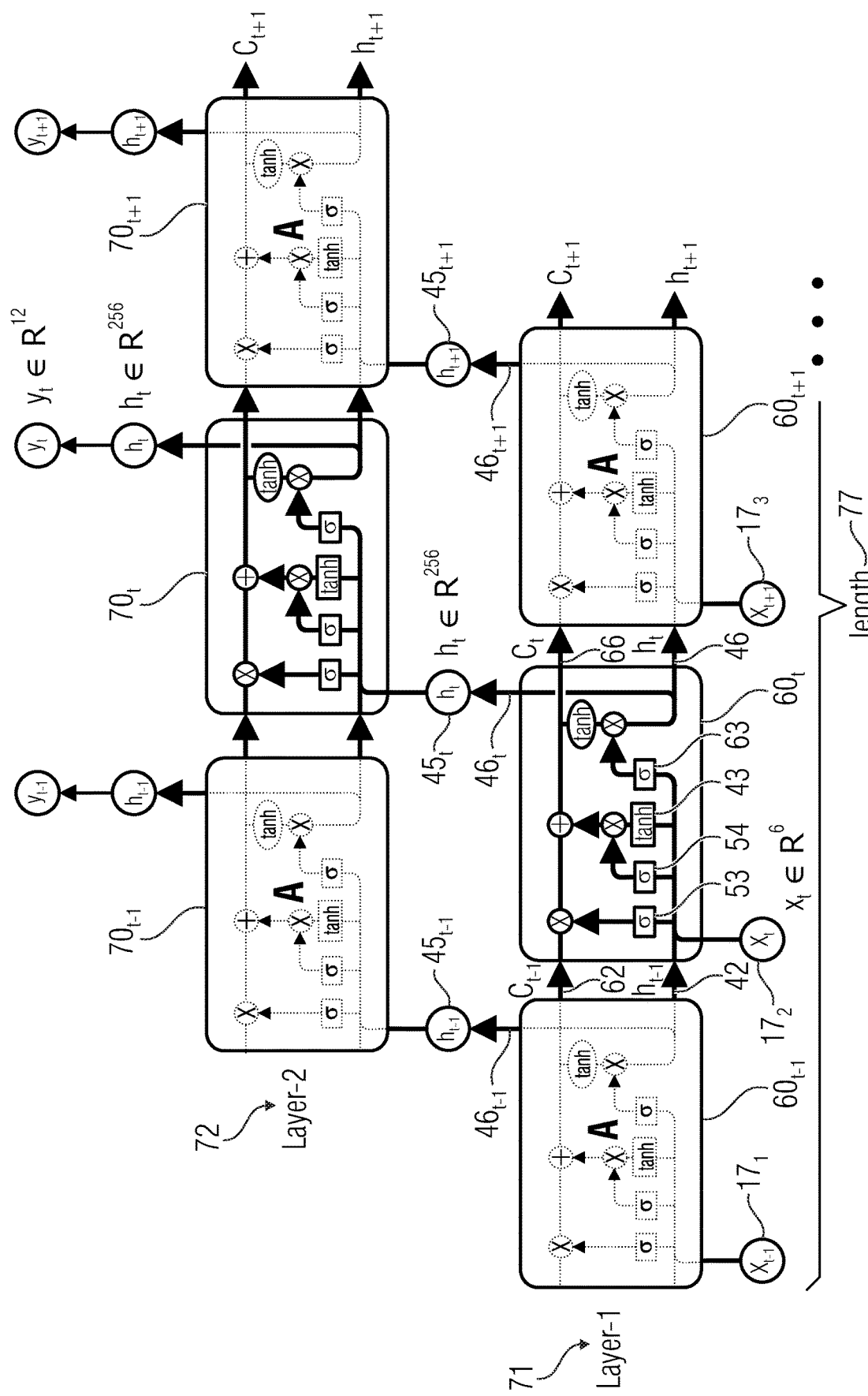
FIG. 7 shows a schematic block diagram of an unrolled LSTM module-based recurrent neural network with two stacked layers of LSTM modules (i.e. a deep LSTM) at different time instances.

FIG. 7 shows a further example, wherein the neural network 18 comprises at least two stacked layers of neural units, namely a first layer 71 and a second layer 72. The first layer 71 comprises at least a first neural unit $60_t$, and the second layer 72 comprises at least a second neural unit $70_t$. The shown stacked structure may be understood to be a deep RNN structure comprising stacked multiple RNN hidden layers.

As can be seen, the sensor data $17_1$, $17_2$, $17_3$ that is acquired at different time instances t−1, t, t+1 is fed as input $X_{t-1}$, $X_t$, $X_{t+1}$ into the respective neural units $60_{t-1}$, $60_t$, $60_{t+1}$ of the first layer 71.

The hidden output vectors $45_{t-1}$, $45_t$, $45_{t+1}$ of each neural unit $60_{t-1}$, $60_t$, $60_{t+1}$ of the first layer 71 may be fed as an input into the respective neural units $70_{t-1}$, $70_t$, $70_{t+1}$ of the second layer 72.

The neural units $60_{t-1}$, $60_t$, $60_{t+1}$ of the first layer 71 and the neural units $70_{t-1}$, $70_t$, $70_{t+1}$ of the second layer 72 may be identical. Alternatively, the internal structure of the neural units $60_{t-1}$, $60_t$, $60_{t+1}$ of the first layer 71 and the neural units $70_{t-1}$, $70_t$, $70_{t+1}$ of the second layer 72 may differ from each other.

According to the embodiment as shown in FIG. 7, the neural network 18 may comprise at least a first layer 71 and a second layer 72, wherein the first layer 71 may comprise a first neural unit $60_t$ and wherein the second layer 72 may comprise a second neural unit $70_t$, wherein at a first time instant t the at least one inertial sensor data $X_t$ is input into the first neural unit $60_t$ of the first layer 71, and wherein an output $h_t$ of the first neural unit $60_t$ is input into the neural unit $70_t$ of the second layer 72. In case of a bi-directional RNN, the intermediate hidden output vectors $45_t$ of each of the separate layers may be fed into the neural units of the next layer.

So far a signal path in a vertical direction, i.e. from a bottom first layer 71 to a top second layer 72 has been described. However, in the embodiment of FIG. 7 also a signal path in a horizontal direction is shown.

As can be seen, the cell state output $C_t$ of a first neural unit $60_t$ at a first time instant t and/or the output $h_t$ 46 of the first neural unit $60_t$ at the first time instant t may be fed as an input into the first neural unit 60 again, namely into the first neural unit $60_{t+1}$ at a subsequent time instant t+1. As already mentioned above, the neural unit 60 itself may be the same neural unit but it may only be depicted in the Figures as a chain of neural units $60_{t-1}$, $60_t$, $60_{t+1}$ for ease of illustration of the states of the neural unit 60 at the different time instances t−1, t, t+1. In other words, the horizontal signal path may describe the signal path of the neural unit 60 at different subsequent time instances t−1, t, t+1. The same holds true for the second layer 72 and any potential further layers.

Accordingly, the depicted subsequent time instances t−1, t, t+1 may represent a length 77 during which the neural network 18 may sample and process the acquired sensor data $17_1$, $17_2$, $17_3$, . . . , $17_n$. Said length 77 may therefore be referred to as a run length, a sample length or a sample period. For example, the sample length 77 may correspond to one second, wherein the time instances t−1, t, t+1 may be fractions of said one second. For example a sample period 77 may have a length of fifty samples, i.e. of fifty time instances. The neural network 18 may run once during a sample period, or the neural network 18 may run permanently over two or more sample periods.

Thus, according to a further embodiment, the neural network 18 may comprise at least a first layer 71 and a stacked second layer 72, wherein the first layer 71 may comprise a first neural unit $60_t$ and wherein the second layer 72 may comprise a second neural unit $70_t$, wherein at a first time instant t the at least one inertial sensor data $X_t$ may be input into the first neural unit $60_t$ of the first layer 71, and wherein at least one output $h_t$ of the first neural unit $60_t$ may be input into the neural unit $70_t$ of the second layer 72. So far it may be the same as described above. However, additionally, at a subsequent second time instant t+1, a second inertial sensor data $X_{t+1}$ and at least one output $h_t$ 46 of the first neural unit $60_t$ at the first time instant t is input into the first neural unit $60_{t+1}$ at the subsequent second time instant t+1.

As mentioned above, several mathematical operations may be executed by the neural network 18, e.g. in the gates 43, 53, 54, 63. In the example shown in FIG. 7 the following mathematical operations may be executed at the different stages:

$$\tilde{h}_j = \sum_{k \in C(j)} h_k,$$

$$i_j = \sigma(W^{(i)}x_j + U^{(i)}\tilde{h}_j + b^{(i)}),$$

$$f_{jk} = \sigma(W^{(f)}x_j + U^{(f)}h_k + b^{(f)}),$$

$$o_j = \sigma(W^{(o)}x_j + U^{(o)}\tilde{h}_j + b^{(o)}),$$

$$u_j = \tanh(W^{(u)}x_j + U^{(u)}\tilde{h}_j + b^{(u)}),$$

$$c_j = i_j \odot u_j + \sum_{k \in C(j)} f_{jk} \odot c_k,$$

$$h_j = o_j \odot \tanh(c_j),$$

wherein (instead of time t the here chosen notation uses j as the running index):

$x_j$ is the input vector;
$i_j$ is the input gate's activation vector;
$f_{jk}$ is the forget gate's activation vector;
$o_j$ is the output gate's activation vector;
$u_j$ is the candidate state vector;
$c_j$ is the cell state vector; and
$h_j$ is the output vector of an LSTM module or neural unit 60, 70.

In this example, the input sensor data $X_t$ may be an element vector $X_t \in \mathbb{R}^6$. For example, it may be an input tensor $X_t \in \mathbb{R}^6$, $[A_x, A_y, A_z, G_x, G_y, G_z]^T$.

Weight matrices W, U and bias vectors b are used in each network layer, wherein in this example:

input weights $W_{xy} \in \mathbb{R}^{6 \times 256}$;
hidden layer weights $U_{xy} \in \mathbb{R}^{256 \times 256}$; and
biases used in the hidden layers $b_x \in \mathbb{R}^{256}$.

The hidden states $h_t$ are also element vectors comprising 256 elements, $h_t \in \mathbb{R}^{256}$.

Furthermore, the cell states $c_t$ are also element vectors comprising 256 elements, $c_t \in \mathbb{R}^{256}$.

As mentioned above, the input inertial sensor data $X_t$ may be an element vector $X_t \in \mathbb{R}^6$ comprising six vector elements, for example an input tensor $X_t \in [A_x, A_y, A_z, G_x, G_y, G_z]^T$. These vector elements $[A_x, A_y, A_z, G_x, G_y, G_z]^T$ may also be referred to as inertial sensor data portions.

According to an embodiment, the at least one inertial sensor data $17_1$ may comprise at least three inertial sensor data portions of the group comprising a linear velocity in x, y and z direction, an angular velocity with respect to the x, y and z axes, a linear acceleration in x, y and z direction, and an angular acceleration with respect to the x, y and z axes.

In other words, the inertial sensor 13 may provide inertial sensor data $17_1$, $17_2$, $17_3$, . . . , $17_n$ at the one or more time instances t−1, t, t+1, wherein the inertial sensor data $17_1$, $17_2$, $17_3$, . . . , $17_n$ may depend on the current orientation and motion of the movable treatment device 11 at one observed time instance t−1, t, t+1. Each of the inertial sensor data $17_1$, $17_2$, $17_3$, $17_n$ may be a vector comprising at least three, or in other examples at least six vector elements, wherein said vector elements represent the above-mentioned inertial sensor data portions, wherein at least one of said inertial sensor data portions may be zero.

Accordingly, the inertial sensor data $17_1$, $17_2$, $17_3$, $17_n$ (vectors), and in particular the sensor data portions (vector elements), may represent the current motion pattern of the movable treatment device 11 as sampled during a sample period 77 comprising one or more subsequent time instances t−1, t, t+1.

According to an embodiment as depicted in FIG. 7, the at least one inertial sensor data $17_2$ (vector) may comprise one or more inertial sensor data portions (vector elements), wherein an input to the neural unit $60_t$ at a first time instant t is a respective inertial sensor data $17_2$ comprising the one or more inertial sensor data portions retrieved during said first time instant t. At least one inertial sensor data $17_1$, $17_2$, $17_3$, $17_n$ may be sampled during a sample time 77.

The neural network 18 may classify the at least one sampled inertial sensor data $17_1$, $17_2$, $17_3$, . . . , $17_n$ which has been sampled during the sample time 77 with respect to at least one motion class $15_1$, $15_2$, $15_3$, . . . , $15_k$ contained in the set 15 of motion classes, as it was initially described with reference to FIG. 1.

As was described, the output vector $y_t$ of the neural network may comprise vector elements that each have a value in a range of between 0 and 1 and where the vector elements sum up to 1 in case the optional softmax function is applied. Each vector element is thus a probability value that the input vector $X_t$ relates to one of the motion classes $15_1$, $15_2$, $15_3$, . . . , $15_k$. The motion pattern classification device 14 may indicate the motion class having received the highest probability value as the motion class to which the input relates. In some embodiments, the motion pattern classification device 14 may indicate no motion class if the highest probability value is below a certain threshold, e.g. below 0.7 (in case of a normalized output). A value below the threshold may be seen to indicate that the prediction quality is low and the outcome not reliable. In some embodiments, the motion pattern classification device 14 may indicate a motion class for a complete sequence of input vectors, where the indicated motion class was identified by applying a maximum criterion or a majority criterion with respect to the sequence of output vectors.

In other words, the neural network 18 may receive the inertial sensor data $17_1, 17_2, 17_3, \ldots, 17_n$ as an input x(t) and it may output one or more probability values as an output y(t). As mentioned above, in the example shown in FIG. 7, the output value y(t) may also be an element vector comprising for example at least three, or at least six, or at least twelve vector elements. Each vector element of the output vector y(t) may represent a probabilistic value for a motion class $15_1, 15_2, 15_3, \ldots, 15_k$ that may be associated with a zone $21_1, 21_2, 21_3, \ldots, 21_m$. That means in case the motion pattern classification device 14 provides a single motion class as output, e.g. by choosing the motion class having the highest probability value above a threshold, the associated one or more zones in which the movable treatment device was used during the sampling period may be indicated to the user, e.g. on a display.

The neural network 18 may receive the at least one inertial sensor data $17_1, 17_2, 17_3, \ldots, 17_n$ and classify the at least one inertial sensor data $17_1, 17_2, 17_3, 17_n$ with respect to at least one motion class $15_1, 15_2, 15_3, \ldots, 15_k$, and since said motion classes $15_1, 15_2, 15_3, \ldots, 15_k$ may each be associated with one or more different zones $21_1, 21_2, 21_3, \ldots, 21_m$ of the target surface 12, the probability values may be seen to indicate how probable it is, that the acquired at least one inertial sensor data $17_1, 17_2, 17_3, 17_n$ corresponds to one of the different zones $21_1, 21_2, 21_3, \ldots, 21_m$ of the target surface 12.

In other words, the apparatus 10 may derive, from the motion pattern classification device 14, an estimation in which zone $21_1, 21_2, 21_3, \ldots, 21_m$ of the target surface 12 the movable treatment device 11 is located by simply receiving sensor data $17_1, 17_2, 17_3, 17_n$ and classifying said sensor data $17_1, 17_2, 17_3, \ldots, 17_n$ with respect to motion classes $15_1, 15_2, 15_3, \ldots, 15_k$ that are each associated with one or more zones $21_1, 21_2, 21_3, \ldots, 21_m$ of the target surface 12.

FIG. 8 shows a block diagram of an example of an inventive method for performing a localization of a movable treatment device 11 relative to a target surface 12, wherein the movable treatment device 11 comprises an inertial sensor 13 and wherein the movable treatment device 11 is configured to treat the target surface 12.

In block 801 the method comprises a step of discriminating between two or more motion classes $15_1, 15_2, 15_3, \ldots, 15_k$ contained in a set 15 of motion classes of the movable treatment device 11. Here, discriminating shall mean that the motion pattern classification device 14 is learned to classify input motion patterns with respect to the two or more motion classes. In other words, two or more motion classes are provided so that a classification can be done.

In block 802 the method comprises a step of receiving at least one inertial sensor data $17_1, 17_2, 17_3, 17_n$ from the inertial sensor 13, the at least one inertial sensor data $17_1, 17_2, 17_3, \ldots, 17_n$ representing a movement of the movable treatment device 11.

In block 803 the method comprises a step of receiving and processing by means of a neural network 18 the at least one inertial sensor data $17_1, 17_2, 17_3, 17_n$ and classifying the at least one inertial sensor data $17_1, 17_2, 17_3, \ldots, 17_n$ with respect to at least one motion class $15_1, 15_2, 15_3, \ldots, 15_k$ contained in the set 15 of motion classes, wherein said motion classes $15_1, 15_2, 15_3, \ldots, 15_k$ contained in the set 15 of motion classes are each associated with one or more different zones $21_1, 21_2, 21_3, \ldots, 21_m$ of the target surface 12 so that the classification of the at least one inertial sensor data $17_1, 17_2, 17_3, \ldots, 17_n$ with the at least one motion class $15_1, 15_2, 15_3, \ldots, 15_k$ indicates an estimation of the location of the movable treatment device 11 with respect to the one or more zones $21_1, 21_2, 21_3, \ldots, 21_m$ of the target surface 12.

Figure 9:
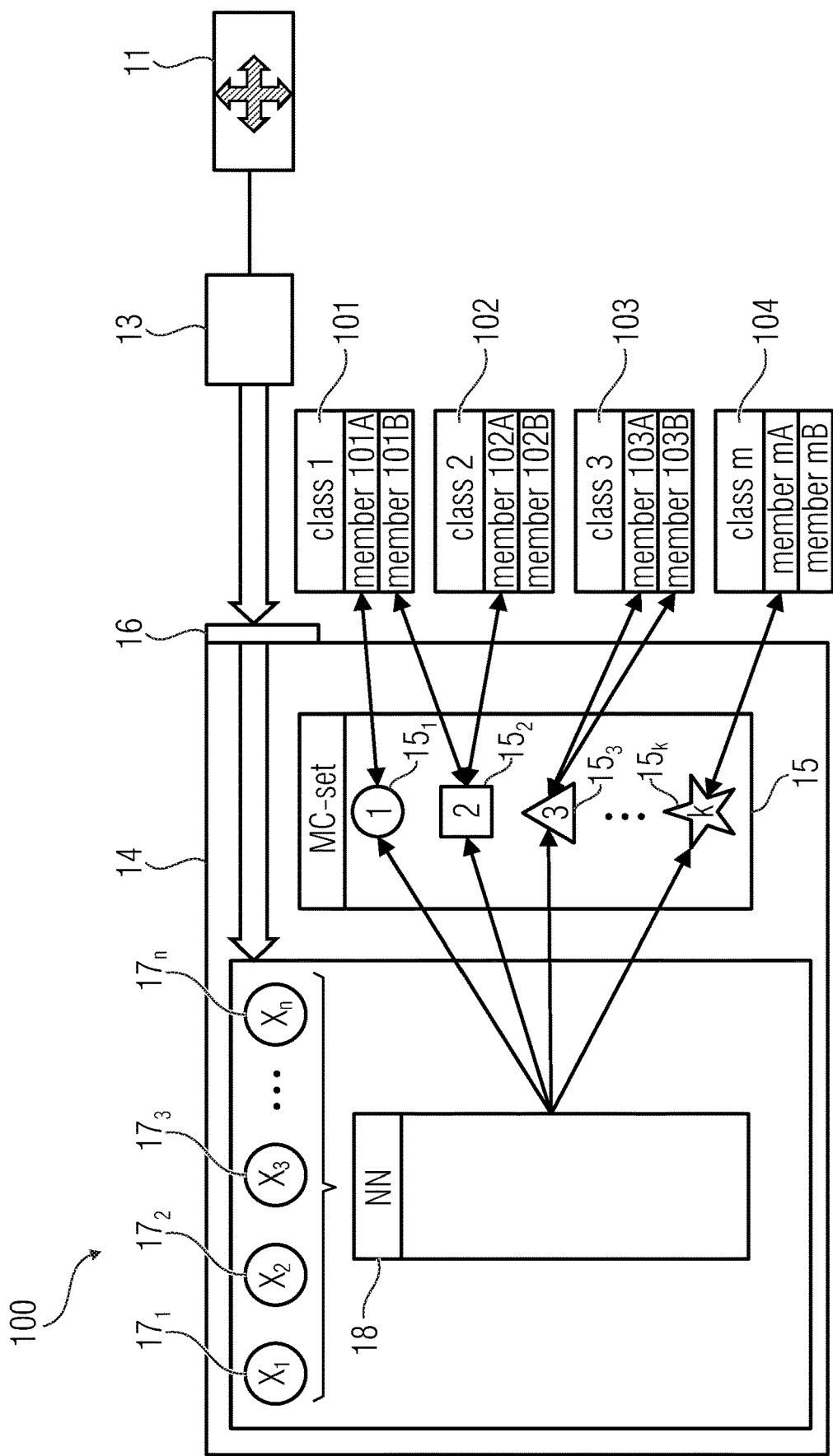
FIG. 9 shows a schematic block diagram of an inventive apparatus according to an embodiment.

FIG. 9 shows an apparatus 100 according to a second aspect of the invention. The apparatus 100 of the second aspect may be like the above-described apparatus 10 of the first aspect. Furthermore, all of the features described above with respect to the apparatus 10 of the first aspect are combinable with the below described apparatus 100 of the second aspect, and vice versa.

The apparatus 100 of the second aspect may vary from the apparatus 10 of the first aspect (c.f. FIG. 1) in that the motion classes $15_1, 15_2, 15_3, \ldots, 15_k$ may be associated with one or more class members 101A, 101B, . . . , mA, mB of one or several associated classes 101, 102, 103, 104 instead of different zones $21_1, 21_2, 21_3, \ldots, 21_m$ of a target surface 12. In essence this is a more abstract and broader discussion of the basic concept discussed with respect to apparatus 10 as an associated class 101 may be anything of relevance. In the following description, a focus is laid on associated classes relating to users, in particular associated class 101 may relate to different members of a user group (e.g. different members of a household) or may relate to users having a different style of using the movable treatment device 11.

Accordingly, the apparatus 100 of the second aspect is configured for classifying a motion of a movable treatment device 11 comprising an inertial sensor 13. The apparatus 100 comprises a motion pattern classification device 14 configured to discriminate between two or more motion classes $15_1, 15_2, 15_3, \ldots, 15_k$ contained in a set 15 of motion classes of the movable treatment device 11.

Furthermore, the apparatus 100 comprises an interface 16 for providing at least one inertial sensor data $17_1, 17_2, 17_3, 17_n$ from the inertial sensor 13 to the motion pattern classification device 14, wherein the at least one inertial sensor data $17_1, 17_2, 17_3, \ldots, 17_n$ represents a motion of the movable treatment device 11.

According to the second aspect of the invention, the motion pattern classification device 14 comprises a neural network 18 that is configured to receive the at least one inertial sensor data $17_1, 17_2, 17_3, 17_n$ and to classify the at least one inertial sensor data $17_1, 17_2, 17_3, 17_n$ to at least one motion class $15_1, 15_2, 15_3, \ldots, 15_k$ contained in the set 15 of motion classes, wherein the at least one classified motion class $15_1, 15_2, 15_3, \ldots, 15_k$ is associated with at least one or more class members 101A, 101B, 102A, 102B, 103A, 103B, mA, mB of one or more associated classes 101, 102, 103, 104 so that the at least one class member 101A, 101B, . . . , mA, mB is selected based on the motion of the movable treatment device 11.

With respect to the classification of input motion patterns, i.e. inertial sensor data $17_1, 17_2, 17_3, \ldots, 17_n$, with respect to motion classes $15_1, 15_2, 15_3, \ldots, 15_k$ contained in a set 15 of motion classes, reference is made to the previous description.

The non-limiting example of FIG. 9 shows four associated classes 101, 102, 103, 104, wherein each associated class comprises two class members 101A, 101B, ..., mA, mB. However, there may be at least one associated class and each associated class may comprise at least two class members. There may also be more than two associated classes or even more than the exemplarily depicted four associated classes.

As can be seen in the example of FIG. 9, a first motion class $15_1$ may be associated with a class member 101A of the first associated class 101. A $k^{th}$ motion class $15_k$ may be associated with a class member mB of the m-th class 104. A second motion class $15_2$ may be associated with two class members of different associated classes, for example with a class member 101B of the first associated class 101 and with a class member 102A of the second associated class 102. A third motion class $15_3$ may be associated with two class members of the same associated class, for example with two class members 103A, 103B of the third associated class.

In the following, some examples of associated classes and class members will be described.

According to an embodiment, at least one associated class 101 of the one or more associated classes 101, 102, 103, 104 may comprise at least one class member 101A, wherein said one associated class 101 may represent a user group, and wherein said at least one class member 101A may represent at least one user of said user group, wherein the at least one motion class $15_1, 15_2, 15_3, \ldots, 15_k$ may be associated with the at least one class member 101A for identifying said at least one user based on the motion of the movable treatment device 11.

In other words, one of the associated classes 101, 102, 103, 104 may represent a user group, i.e. a group of users using the movable treatment device 11. The respective associated class may comprise at least one class member that may represent one particular user of said user group. For example, the first class 101 may represent a user group, wherein said user group may relate to the individuals of a single household. In this example, the user group 101 may only contain one class member 101A, i.e. one person. The inventive apparatus 100 may be configured to identify said at least one user 101A simply based on the motion of the movable treatment device 11. Thus, the apparatus 100 may personalize any actions or interactions with said one identified user 101A, as will be described with some examples later.

According to a further embodiment, at least one associated class 101 of the one or more associated classes 101, 102, 103, 104 may comprise at least two class members 101A, 101B, wherein said one associated class 101 may represent a user group, and wherein said at least two class members 101A, 101B may represent at least two users of said user group, wherein the at least one motion class $15_1, 15_2, 15_3, \ldots, 15_k$ may be associated with one of said at least two class members 101A, 101B for identifying at least one user within the user group based on the motion of the movable treatment device 11.

In other words, one of the associated classes 101, 102, 103, 104 may represent a user group, i.e. a group of users using the movable treatment device 11. The respective associated class may comprise at least one class member that may represent one particular user of said user group. For example, the first associated class 101 may represent a user group, wherein said user group may be a family. The class members 101A, 101B of said associated class 101 may represent the family members. For example, the user group 101 may comprise one or more family members, wherein a first class member 101A may represent the mother of the family and a second class member 101B may represent a child of the family.

The apparatus 100 may be configured to identify at least one user simply based on the motion of the movable treatment device 11. This may be achieved if every user may use the movable treatment device 11 in a different or individual way.

For example, in an embodiment the movable treatment device 11 is a movable oral care device, such as a toothbrush, in particular an electric toothbrush. The movable oral care device may also be at least one of a dental floss, a plaque removing device, an ultrasound device and a waterjet device.

To take up the example above, the mother 101A may use the toothbrush 11 in a different way than the child 101B. The inertial sensor 13 of the toothbrush 11 may provide its inertial sensor data $17_1, 17_2, 17_3, 17_n$ to the motion pattern classification device 14 comprising the neural network 18.

The neural network 18 may classify the inertial sensor data $17_1, 17_2, 17_3, 17_n$ with respect to at least one motion class $15_1, 15_2, 15_3, \ldots, 15_k$ as was already described.

For example, as shown in FIG. 9, the mother may have a brushing style that corresponds to the first motion class $15_1$. This motion class $15_1$ may be associated with class member 101A that represents the mother. The child instead may have a different brushing style than the mother, for example a brushing style that corresponds to the second motion class $15_2$. This motion class $15_2$ may be associated with class member 101B that represents the child.

Thus, the inventive apparatus 100 may identify a user of a user group simply based on the different motion pattern of the movable treatment device 11. As mentioned above, the inventive apparatus 100 may personalize any action or interaction with the identified user.

According to an embodiment, the motion pattern classification device 14 may be configured to select, based on the step of identifying said at least one user 101A, a user-specific set 115 comprising two or more user-specific motion classes $115_1, 115_2, 115_3, \ldots, 115_k$ of the movable treatment device 11 which are characteristic for said identified at least one user 101A.

Figure 10:
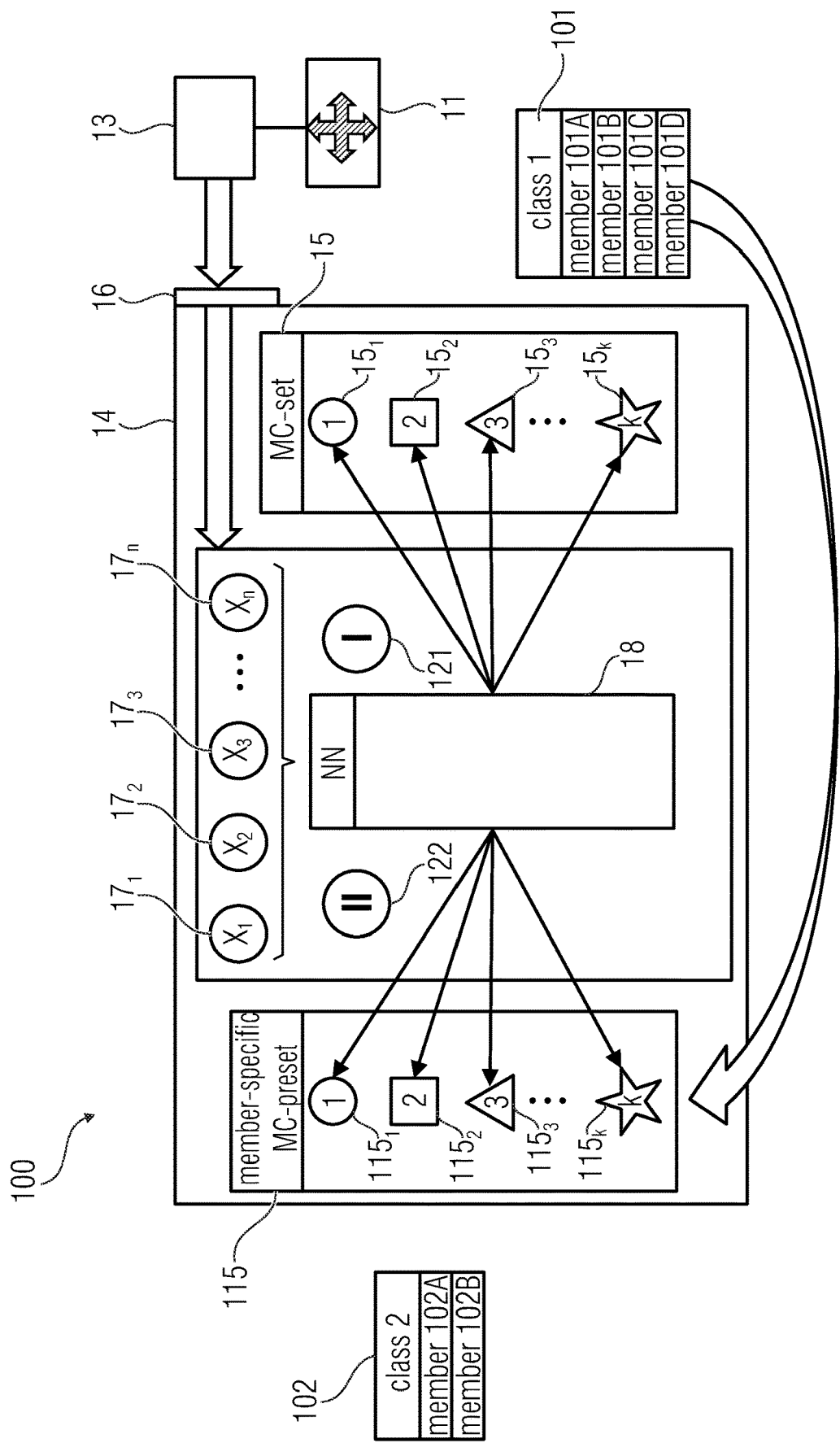
FIG. 10 shows a schematic block diagram of an inventive apparatus according to a further embodiment.

An example of this two-step process is shown in FIG. 10. In a first step 121, a user is identified. The identified user may be associated with a user-specific set 115 of motion classes $115_1, 115_2, 115_3, \ldots, 115_k$ that have been individually trained by the neural network 18 using individualized labelled training data. In a second step 122 the neural network 18 uses the user-specific motion classes $115_1, 115_2, 115_3, \ldots, 115_k$ from the user-specific set 115. In other words, the neural network 18 may then use weights and biases that are associated with the particular user instead of weights and biases that are valid for a broader population. Thus, the inventive apparatus 100 may act and interact with each identified user individually.

In FIG. 10 a first step 121 is shown in which the neural network 18 receives the at least one inertial sensor data $17_1, 17_2, 17_3, \ldots, 17_n$ and classifies same with respect to at least one of the motion classes $15_1, 15_2, 15_3, \ldots, 15_k$ that are contained in the set 15 of motion classes. The at least one classified motion class, for example the $k_{th}$ motion class $15_k$, may be associated with a class member 101B of a first associated class 101. This procedure may correspond to the procedure as described above with reference to FIG. 9.

The associated class 101 may relate to a user group and the class member 101B may be a particular user of said user group. To take up the above example, the identified user 101B may be the child of the family. The apparatus 100 may have stored user-specific motion classes. That is, the identified user, i.e. the child 101B, may have its own individual user-specific set 115 of motion classes $115_1$, $115_2$, $115_3$, . . . , $115_k$ stored in the apparatus 100. For any further actions following the identification in the first step 121, the motion pattern classification device 14, and in particular the neural network 18, may use these user-specific motion classes $115_1$, $115_2$, $115_3$, . . . , $115_k$ belonging to the previously identified user. As was stated before, the reference to motion classes means that a user-specific set of weights and biases will be used by the neural network 18, which weights and biases were trained by using user-specific labelled input data.

Thus, the neural network 18 may select, after the step 121 of identifying said at least one user 101B, at least one user-specific set 115 comprising two or more user-specific motion classes $115_1$, $115_2$, $115_3$, . . . , $115_k$ of the movable treatment device 11 which are characteristic for said identified at least one user 101B.

Accordingly, in a second step 122 following the first step 121 of identifying the user, the neural network 18 may use the user-specific set 115 of user-specific motion classes $115_1$, $115_2$, $115_3$, . . . , $115_k$ in replacement of the set 15 of motion classes $15_1$, $15_2$, $15_3$, . . . , $15_k$. That is, all of the herein described actions that can be executed by the apparatuses 10, 100 by exploiting the set 15 of motion patterns $15_1$, $15_2$, $15_3$, . . . $15_k$ can also be executed individualized or personalized for each identified user by the apparatuses 10, 100 by exploiting the user-specific set 115 of motion classes $115_1$, $115_2$, $115_3$, . . . $115_k$ instead of the set 15 of motion patterns $15_1$, $15_2$, $15_3$, . . . $15_k$.

Thus, according to an embodiment the neural network 18 may be configured to replace, after the first step 121 of identifying said at least one user 101B, the set 15 of motion classes by the selected user-specific set 115, and to replace the two or more motion classes $15_1$, $15_2$, $15_3$, . . . , $15_k$ contained in the set 15 of motion patterns by the two or more user-specific motion classes $115_1$, $115_2$, $115_3$, . . . , $115_k$ contained in the user-specific motion pattern preset 115. It is noted that the motion classes $15_1$, $15_2$, $15_3$, . . . , $15_k$ were chosen to predict the user that moves the movable treatment device, but the motion classes $115_1$, $115_2$, $115_3$, . . . , $115_k$ may have been chosen for a different task such as a localization of the movable treatment device 11.

Figure 11:
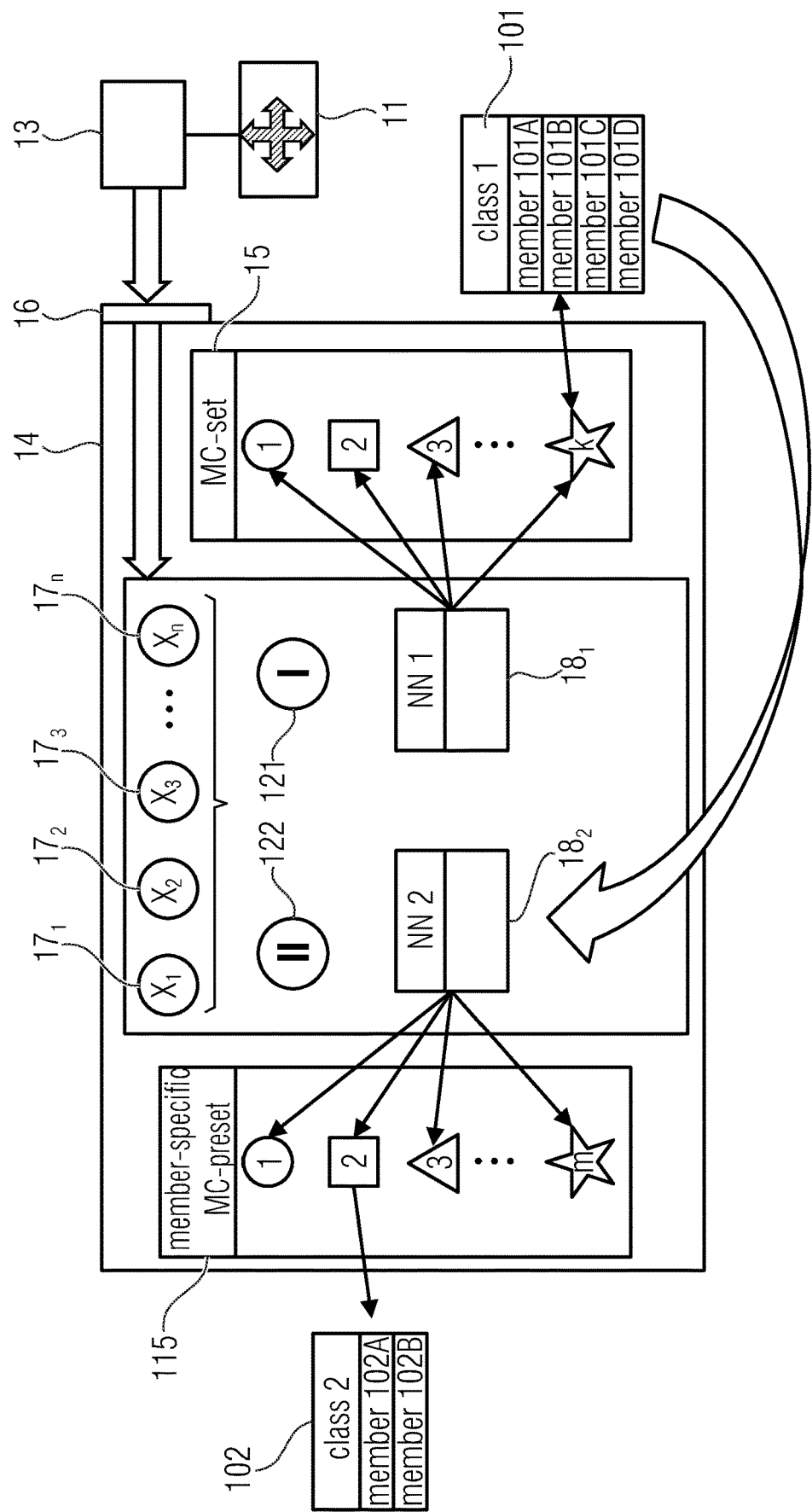
FIG. 11 shows a schematic block diagram of an inventive apparatus according to a further embodiment.

Additionally or alternatively, the apparatus 100 may comprise at least a second neural network. FIG. 11 shows such an example.

The example of the apparatus 100 of FIG. 11 may substantially correspond to the apparatus 100 of the example shown in FIG. 10. The apparatus of FIG. 11 differs from the apparatus of FIG. 10 in that the apparatus of FIG. 11 may comprise a second neural network $18_2$. It shall be understood that while it was explained with reference to FIG. 10 that the structurally same neural network 18 is used for the two different classification tasks and that only the weights and biases might be changed, the present example uses two different neural networks that differ in their structure, which allows using optimized neural network structures for each classification task.

As can be seen in FIG. 11, in a first step 121 a first neural network $18_1$ may execute the actions as described above, for example identifying a user 101B of a user group 101. However, in a second step 122, the inertial sensor data $17_1$, $17_2$, $17_3$, . . . , $17_n$ may be fed into said second neural network $18_2$. The second neural network $18_2$ may use a user-specific set 115 of motion classes $115_1$, $115_2$, $115_3$, . . . , $115_k$ as described above. Obviously, at least two different sets 115 of motion classes $115_1$, $115_2$, $115_3$, . . . , $115_k$ must be stored in the apparatus in order to allow running the second neural network with one set of motion classes optimized for one user and another set of motion classes optimized for another user.

In other words, after the first step 121 of identifying said at least one user 101B, the motion pattern classification device 14 may use the second neural network $18_2$, wherein the second neural network $18_2$ may be configured to receive the at least one inertial sensor data $17_1$, $17_2$, $17_3$, . . . , $17_n$ and to classify the at least one inertial sensor data $17_1$, $17_2$, $17_3$, . . . , $17_n$ with respect to at least one user-specific motion class $115_1$, $115_2$, $115_3$, . . . , $115_k$ contained in the user-specific set 115 of motion classes, wherein said user-specific motion classes $115_1$, $115_2$, $115_3$, . . . , $115_k$ may each be associated with at least one class member 102A, 102B of an associated class 102 so that the at least one class member 102A, 102B is selected based on the motion of the movable treatment device 11. The associated class 102 may relate to the target surface and the class members are the zones of the target surface.

Accordingly, the motion pattern classification device 14 may be configured to use the user-specific set 115 of user-specific motion classes $115_1$, $115_2$, $115_3$, . . . , $115_k$ for user-specifically classifying the motion of the movable treatment device 11 by means of the at least one inertial sensor data $17_1$, $17_2$, $17_3$, . . . , $17_n$.

As shown in the examples of FIGS. 10 and 11, the apparatus 100 may comprise at least one associated class 102 for classifying purposes in the second step 122. However, the apparatus 100 may comprise more than one associated class, as shown in the example of FIG. 9, in the second step 122.

In said second step 122, for example after having identified a particular user in the first step 121, different actions may be performed by the movable treatment device 11. For example, the movable treatment device 11 may change its operation mode based on the identified user. For example, the movable treatment device 11 may be electrically driven and it may comprise a motor, wherein the movable treatment device 11 may change one or more motor specific characteristics, such as frequency, amplitude or pulsation, based on the identified user. Additionally or alternatively, the movable treatment device 11 may comprise one or more elements for communicating with or providing feedback to a user, for example a visual element, such as a light, e.g. a LED, or a haptical element, such as a vibrational motor. For example, the movable treatment device 11 may change a user experience based on the identified user by changing the operation mode of said elements for communicating, for instance by changing LED lights to a different color or by providing differently pulsed feedback by the vibrational motor, based on the identified user.

Additionally or alternatively to identifying a particular user of a user group, for example, a family member of a family, the apparatus 100 may be configured to identify a particular user type. For example, if the movable treatment device 11 was a toothbrush, some people start brushing their teeth with their front teeth or incisors while some other people may start brushing their teeth with their back teeth or molars. In a further example, if the personal appliance was a razor, some people may shave with the grain while some other people may shave against the grain Summarizing a user type may be a type of user who uses the movable treatment device 11 in a particular way. There may be two or more users that can be clustered into groups of user types. The previously described example of user identification instead identifies each user individually.

According to an embodiment for identifying user types, at least one associated class 104 of the one or more associated classes 101, 102, 103, 104 may comprise at least two class members nA, nB, wherein said one associated class 104 may represent a user type of the movable treatment device 11, wherein a first class member nA may represent a first user type of the movable treatment device 11 and wherein a second class member nB may represent a second user type of the movable treatment device 11, wherein the at least one motion class $15_1$, $15_2$, $15_3$, . . . , $15_k$ may be associated with either the first or the second class member mA, mB for identifying a user type of the movable treatment device 11 based on the motion of the movable treatment device 11.

According to a further embodiment, the motion pattern classification device 14 may be configured to select, after the step of identifying said user type, a user type specific set 115 comprising two or more user type specific motion classes $115_1$, $115_2$, $115_3$, . . . , $115_k$ of the movable treatment device 11 which are characteristic for said identified user type, and wherein the neural network 18 may be configured to replace, after the step of identifying said user type, the set 15 of motion classes by the selected user type specific set 115 and to replace the two or more motion classes $15_1$, $15_2$, $15_3$, . . . , $15_k$ contained in the set 15 of motion classes by the two or more user type specific motion classes $115_1$, $115_2$, $115_3$, . . . , $115_k$.

Everything that has been explained above with respect to the user-specific set 115 of user-specific motion classes $115_1$, $115_2$, $115_3$, . . . , $115_k$ also holds true for the user type specific set 115 of user type specific motion classes $115_1$, $115_2$, $115_3$, . . . , $115_k$.

As mentioned above, the identified user types may be clustered into a cluster or group of user types. Therefore, the apparatus 100 may perform a cluster analysis in which a user may use the movable treatment device 11 for a predetermined number of times before this user is clustered into a particular user type group. For example, a user may use its razor five times on five subsequent days. On four out of the five days the user may shave against the grain. Thus, after the fifth day the apparatus 100 may cluster this user into a user type group in which all users shaving against the grain are clustered.

The cluster analysis may also be performed at shorter time intervals, i.e. switching the toothbrush 11 on and off may be done directly successively. For example, the user may switch on his electric toothbrush 11 a first time, switch it off, and switch it on a second time to restart the toothbrush 11 again. At the time of restarting the toothbrush 11, the inventive apparatus 100, and in particular the neural network 18, may also be restarted. When the toothbrush 11 is switched on, it may collect information for the cluster analysis. However, at least the neural network 18 shall restart every time before new information for the cluster analysis is collected Summarizing, the apparatus 100 may repeatedly (e.g. five times) perform the cluster analysis before finally clustering the user into a particular user type group.

After the user has been clustered into a particular user type specific group, the neural network 18 may use the associated user type specific preset 115 of user type specific motion patterns $115_1$, $115_2$, $115_3$, . . . , $115_k$.

According to such an embodiment, the motion pattern classification device 14 may be configured to repeatedly perform a cluster analysis for a predetermined number of times, wherein in each said cluster analysis the neural network 18 may be configured to restart and to perform, after the restart, the step of receiving the at least one inertial sensor data $17_1$, $17_2$, $17_3$, . . . , $17_n$ and to map the at least one inertial sensor data $17_1$, $17_2$, $17_3$, . . . , $17_n$ to at least one motion pattern $15_1$, $15_2$, $15_3$, . . . , $15_k$ contained in the set 15 of motion patterns, and wherein the neural network 18 may be configured to select the user type specific motion pattern preset 115 after performing the cluster analysis for the predetermined number of times.

The apparatus 100 may allow even more scenarios for classifying a motion of the movable treatment device 11. Therefore, reference shall be made to FIG. 9 again.

According to an embodiment, at least one class 102 of the one or more associated classes 101, 102, 103, 104 may comprise at least two class members 102A, 102B, wherein said one associated class 102 may represent a handling evaluation of the movable treatment device 11, wherein a first class member 102A may represent a correct handling of the movable treatment device 11 and wherein a second class member 102B may represent a wrong handling of the movable treatment device 11, wherein the at least one classified motion class $15_1$, $15_2$, $15_3$, . . . , $15_k$ may be associated with either the first or the second class member 102A, 102B for evaluating the handling of the movable treatment device 11 based on the motion of the movable treatment device 11. In accordance with an example, two or more motion classes $15_1$, $15_2$, $15_3$, . . . , $15_k$ may relate to correct handling of the device and these motion classes may thus be associated with the first class member 102A and two or more motion classes $15_1$, $15_2$, $15_3$, . . . , $15_k$ may relate to incorrect handling of the device and these motion classes may thus be associated with the second class member 102B.

In other words, the apparatus 100 may be configured to check whether a user of the movable treatment device 11 uses the movable treatment device 11 correctly or not. Of course, said one class 102 representing the handling evaluation may also be used as a class in the second step 122 of the above-described two-step procedures of FIGS. 10 and 11, e.g. after identifying a user and/or a user type.

According to a further embodiment at least one associated class 103 of the one or more associated classes 101, 102, 103, 104 may comprise at least two class members 103A, 103B, wherein said one associated class 103 may represent a quality of motion execution of the movable treatment device 11, wherein a first class member 103A may represent a good motion execution of the movable treatment device 11 and wherein a second class member 103B may represent a bad motion execution of the movable treatment device 11, wherein the at least one classified motion class $15_1$, $15_2$, $15_3$, . . . , $15_k$ may be associated with either the first or the second class member 103A, 103B for evaluating a quality of motion execution of the movable treatment device 11 based on the motion of the movable treatment device 11.

In other words, the apparatus 100 may be configured to check whether a user of the movable treatment device 11 may use the movable treatment device 11 in a good way or in a bad way. A good way may be a way of performing the motion of the movable treatment device 11 as intended, while a bad way may be a way of performing the motion of the movable treatment device 11 as not intended. For example, if the movable treatment device 11 was a toothbrush, then the apparatus may check whether the user may have a good or a bad brushing technique.

Of course, said one class 103 representing the quality of motion execution may also be used as an associated class in the second step 122 of the above-described two-step procedures of FIGS. 10 and 11, e.g. after identifying a user and/or a user type.

The neural network 18 of the apparatus 100 may comprise the same or similar features as the neural network 18 of the apparatus 10 that has been described with reference to FIGS. 4 to 7.

Everything that has been described above with respect to any features of the neural network 18 of the apparatus 10 as shown in FIGS. 4 to 7 also holds true for the neural network 18 of the apparatus 100 as described with reference to FIGS. 9 to 11.

Figure 12:
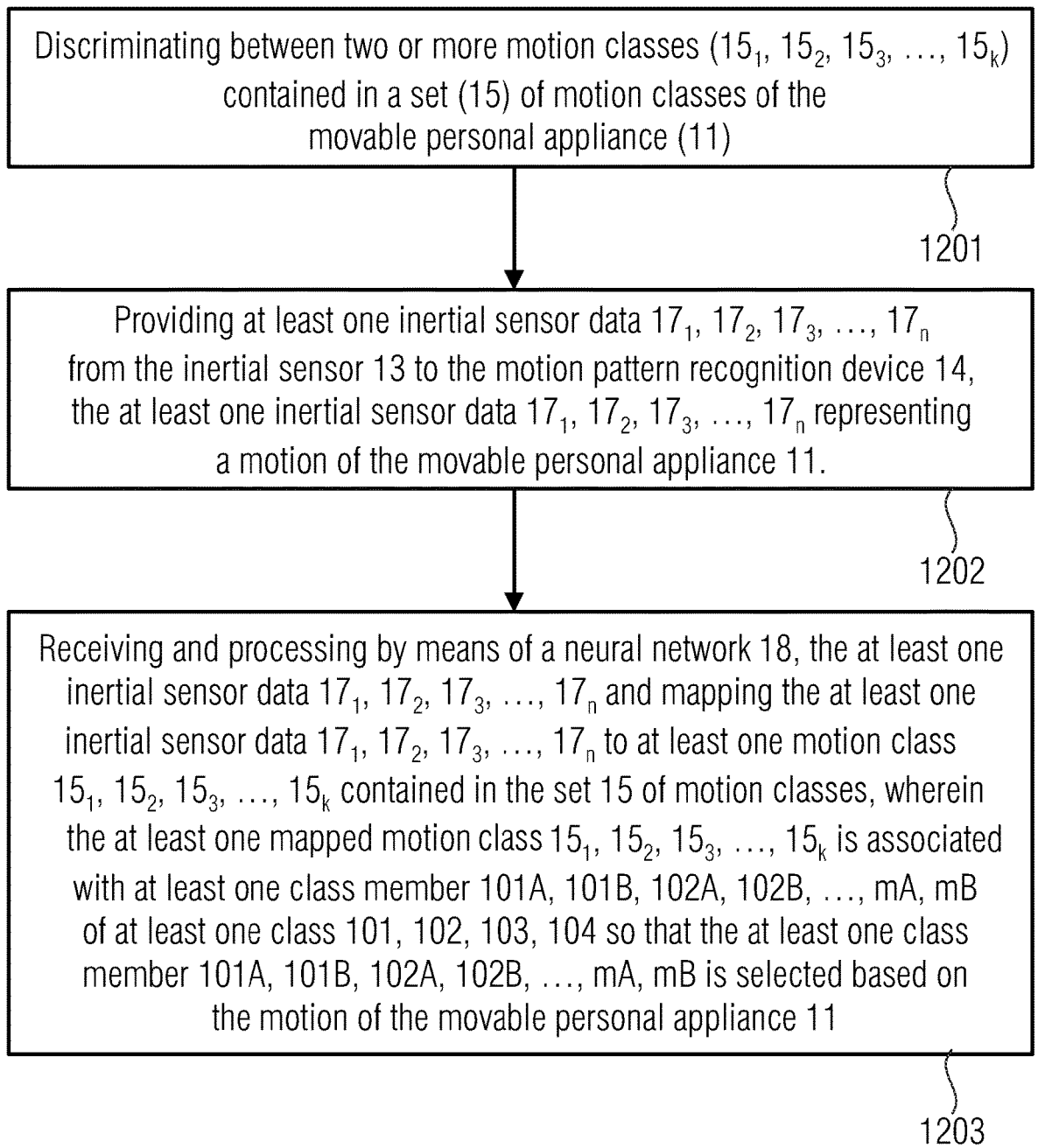
FIG. 12 shows a block diagram of an inventive method according to an embodiment.

FIG. 12 shows a block diagram of an inventive method for classifying a motion of a movable treatment device 11 that comprises an inertial sensor 13.

In block 1201 the method comprises a step of discriminating between two or more motion classes $15_1$, $15_2$, $15_3$, ..., $15_k$ contained in a set 15 of motion patterns of the movable treatment device 11.

In block 1202 the method comprises a step of providing at least one inertial sensor data $17_1$, $17_2$, $17_3$, ..., $17_n$ from the inertial sensor 13 to the motion pattern classification device 14, the at least one inertial sensor data $17_1$, $17_2$, $17_3$, ..., $17_n$ representing a motion of the movable treatment device 11.

In Block 1203 the method comprises a step of receiving and processing, by means of a neural network 18, the at least one inertial sensor data $17_1$, $17_2$, $17_3$, ..., $17_n$ and classifying the at least one inertial sensor data $17_1$, $17_2$, $17_3$, ..., $17_n$ with respect to at least one motion class $15_1$, $15_2$, $15_3$, ..., $15_k$ contained in the set 15 of motion classes, wherein the at least one classified motion class $15_1$, $15_2$, $15_3$, ..., $15_k$ is associated with at least one class member 101A, 101B, 102A, 102B, ..., mA, mB of at least one associated class 101, 102, 103, 104 so that the at least one class member 101A, 101B, 102A, 102B, ..., mA, mB is selected based on the motion of the movable treatment device 11.

According to yet a further example of the inventive apparatus 10, 100 the movable treatment device 11 may be a personal appliance and the target surface 12 may be a body portion to be treated by the movable treatment device 11.

According to yet a further example of the inventive apparatus 10, 100 the movable treatment device 11 or the movable treatment device 11 may comprise a pressure sensor for sensing a pressure applied onto a target zone by the personal appliance and/or a load sensor for sensing a motor load of a motor that may drive the personal appliance.

Respective sensor data of the pressure sensor and/or the load sensor may be fed as input into the neural unit 18, in addition or alternatively to the at least one inertial sensor data $17_1$, $17_2$, $17_3$, ..., $17_n$.

According to yet a further example of the inventive apparatus 10, the apparatus 10 may comprise an output interface for outputting to a user the one or more zones $21_1$, $21_2$, $21_3$, ..., $21_m$ of the target surface 12 in which the movable treatment device 11 is located.

According to yet a further example of the inventive apparatus 100, the apparatus 100 may comprise an output interface for outputting information to a user, said information being related to the one or more associated classes 101, 102, 103, 104 and/or to the one or more class members 101A, 101B, ..., mA, mB of the one or more associated classes 101, 102, 103, 104.

In each of the herein described embodiments, sensor data $17_1$, $17_2$, $17_3$, ..., $17_n$ can be stored on the movable treatment device or treatment device 11 and later on can be fed into the apparatus 10, 100, in a way as described above. Any post processing of this stored sensor data $17_1$, $17_2$, $17_3$, ..., $17_n$ with respect to different zones or associated classes may be used to show a consumer or user on a dashboard how well and what zones they covered, what they forgot, what was in target vs out of target. This data may be shown per usage and/or may be aggregated over two and more uses over time (i.e. show the consumer or user a simple dashboard of how they have been brushing over the week).

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a microprocessor, a programmable computer or an electronic circuit. In some embodiments, one or more of the most important method steps may be executed by such an apparatus.

Depending on certain implementation requirements, embodiments of the invention can be implemented in hardware or in software or at least partially in hardware or at least partially in software. The implementation can be performed using a digital storage medium, for example a floppy disk, a DVD, a Blu-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may for example be stored on a machine-readable carrier.

Other embodiments comprise the computer program for performing one of the methods described herein, stored on a machine-readable carrier.

In other words, an embodiment of the inventive method is, therefore, a computer program having a program code for performing one of the methods described herein, when the computer program runs on a computer.

A further embodiment of the inventive methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitory.

A further embodiment of the inventive method is, therefore, a data stream or a sequence of signals representing the computer program for performing one of the methods described herein. The data stream or the sequence of signals may for example be configured to be transferred via a data communication connection, for example via the Internet, via Bluetooth Low Energy (BLE), via WiFi, or via any kind of network, for instance via a meshed network.

A further embodiment comprises a processing means, for example a computer, or a programmable logic device, configured to or adapted to perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

The apparatus described herein may be implemented using a hardware apparatus, or using a computer, or using a combination of a hardware apparatus and a computer.

The methods described herein may be performed using a hardware apparatus, or using a computer, or using a combination of a hardware apparatus and a computer.

The above-described embodiments are merely illustrative for the principles of the present invention. It is understood that modifications and variations of the arrangements and the details described herein will be apparent to others skilled in the art. It is the intent, therefore, to be limited only by the scope of the impending patent claims and not by the specific details presented by way of description and explanation of the embodiments herein.

Furthermore, the dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus (10; 100) for performing a localization of a movable treatment device (11) relative to a target surface (12), the movable treatment device (11) comprising at least one inertial sensor (13) and being configured to treat the target surface (12), the apparatus (10) comprising:
    a motion pattern classification device (14) configured to discriminate between two or more motion classes ($15_1$, $15_2$, $15_3$, . . . , $15_k$) contained in a set (15) of motion classes of the movable treatment device (11), and
    an interface (16) for providing at least one inertial sensor data ($17_1$, $17_2$, $17_3$, . . . , $17_n$) from the inertial sensor (13) to the motion pattern classification device (14), the at least one inertial sensor data ($17_1$, $17_2$, $17_3$, . . . , $17_n$) representing a movement of the movable treatment device (11),
    wherein the motion pattern classification device (14) comprises at least one neural network (18) configured to receive the at least one inertial sensor data ($17_1$, $17_2$, $17_3$, . . . , $17_n$) and to classify the at least one inertial sensor data ($17_1$, $17_2$, $17_3$, . . . , $17_n$) with respect to the motion classes ($15_1$, $15_2$, $15_3$, . . . , $15_k$) contained in the set (15) of motion classes, wherein said motion classes ($15_1$, $15_2$, $15_3$, . . . , $15_k$) are each associated ($20_1$, $20_2$, $20_3$, . . . , $20_k$) with one or more different zones ($21_1$, $21_2$, $21_3$, . . . , $21_m$) relating to the target surface (12) so that the classification of the at least one inertial sensor data ($17_1$, $17_2$, $17_3$, . . . , $17_n$) with respect to the motion classes ($15_1$, $15_2$, $15_3$, . . . , $15_k$) indicates an estimation of the location of the movable treatment device (11) with respect to the one or more zones ($21_1$, $21_2$, $21_3$, . . . , $21_m$) of the target surface (12),
    wherein an output ($y_{t-1}$; $y_t$; $y_{t+1}$) of the neural network (18) comprises one or more probability or likelihood values for the estimation of the location of the movable treatment device (11) with respect to the one or more zones ($21_1$, $21_2$, $21_3$, . . . , $21_m$) of the target surface (12),
    wherein performance of the localization does not use input from a camera.

2. The apparatus (10; 100) of claim 1, wherein the apparatus (10) is arranged to indicate one zone ($Z_3$) in which the movable treatment device (11) is located based on the highest probability or likelihood value of the output ($y_{t-1}$; $y_t$; $y_{t+1}$).

3. The apparatus (10; 100) of claim 1, wherein at least one motion class ($15_{NB}$) contained in the set (15) of motion classes is associated with a zone ($21_{NB}$) outside the target surface (12), wherein the classification of the at least one inertial sensor data ($17_1$, $17_2$, $17_3$, . . . , $17_n$) with respect to this motion class ($15_{NB}$) indicates that the movable treatment device (11) is located in said zone ($21_{NB}$) outside the target surface (12).

4. The apparatus (10; 100) of claim 1, wherein the neural network (18) is a recurrent neural network, in particular a long short-term memory network or a gated recurrent unit network, further in particular where the recurrent neural network is a bi-directional recurrent neural network and even further in particular wherein the recurrent neural network is at least a two-layer, bi-directional recurrent neural network.

5. The apparatus (10; 100) of claim 1, wherein the interface (16) is arranged to provide a sequence of inertial sensor data ($17_1$, $17_2$, $17_3$, . . . , $17_n$) from the inertial sensor (13) to the motion pattern classification device (14) as an input ($X_1$, $X_2$, $X_3$, . . . , $X_n$).

6. The apparatus (10) of claim 5, wherein the apparatus (10) is arranged to indicate one or more of the zones ($21_1$, $21_2$, $21_3$, ..., $21_m$) in which the movable treatment device was located during the time period relating to the sequence of inertial sensor data based on a maximum criterion or a majority criterion.

7. The apparatus (10) of claim 1, wherein the at least one inertial sensor data ($17_1$, $17_2$, $17_3$, ..., $17_n$) comprises at least one inertial sensor data portion, in particular at least three inertial sensor portions of the group comprising a linear velocity in x, y and z direction, an angular velocity with respect to the x, y and z axes, a linear acceleration in x, y and z direction, and an angular acceleration with respect to the x, y and z axes.

8. The apparatus (10) of claim 1, wherein the movable treatment device (11) comprises at least one further sensor such as a pressure sensor arranged for measuring the pressure with which the treatment device (11) is applied against the target surface or a load sensor for sensing a motor load of a motor driving the movable treatment device (11) and the interface (16) is arranged for providing at least one further sensor data from the further sensor to the motion pattern classification device (14) in addition to the at least one inertial sensor data ($17_1$, $17_2$, $17_3$, ..., $17_n$).

9. The apparatus (10) of claim 1, wherein the motion pattern classification device (14) comprises at least a first and a second neural network (18) that are each configured to receive the at least one inertial sensor data ($17_1$, $17_2$, $17_3$, ..., $17_n$) and the first neural network is configured to classify the at least one inertial sensor data ($17_1$, $17_2$, $17_3$, ..., $17_n$) with respect to motion classes ($15_1$, $15_2$, $15_3$, ..., $15_k$) contained in a first set (15) of motion classes and the second neural network is configured to classify the at least one inertial sensor data ($17_1$, $17_2$, $17_3$, ..., $17_n$) with respect to motion classes ($15_1$, $15_2$, $15_3$, ..., $15_k$) contained in a second set (15) of motion classes, wherein said motion classes ($15_1$, $15_2$, $15_3$, ..., $15_k$) of the first and second set of motion classes are each associated ($20_1$, $20_2$, $20_3$, ..., $20_k$) with one or more different zones ($21_1$, $21_2$, $21_3$, ..., $21_m$) relating to the target surface (12) so that the classification of the at least one inertial sensor data ($17_1$, $17_2$, $17_3$, ..., $17_n$) with respect to the motion classes ($15_1$, $15_2$, $15_3$, ..., $15_k$) indicates an estimation of the location of the movable treatment device (11) with respect to the one or more zones ($21_1$, $21_2$, $21_3$, ..., $21_m$) of the target surface (12) and wherein an output ($y_{t-1}$; $y_t$; $y_t+1$) of the first neural network and an output ($y_{t-1}$; $y_t$; $y_{t+1}$) of the second neural network are used to provide an estimation of the location of the movable treatment device (11) with respect to the one or more zones ($21_1$, $21_2$, $21_3$, ..., $21_m$) of the target surface (12).

10. The apparatus (10) of claim 1, wherein the neural network comprises trained weight matrices and bias vectors.

11. The apparatus (10) of claim 1, wherein the movable treatment device (11) is a personal appliance and the target surface (12) is a body portion to be treated by the movable treatment device (11).

12. The apparatus (10) of claim 1, wherein the movable treatment device (11) is an oral care device and the target surface (12) is an oral cavity, wherein the oral cavity (12) is separated into a plurality of oral cavity zones ($1a$-$9a$; $1b$-$16b$), wherein the classification of the at least one inertial sensor data ($17_1$, $17_2$, $17_3$, ..., $17_n$) with respect to the motion classes ($15_1$, $15_2$, $15_3$, ..., $15_k$) indicates an estimation of the location of the oral care device (11) with respect to the one or more oral cavity zones ($1a$-$9a$; $1b$-$16b$).

13. A system comprising an apparatus (10) of claim 1 and a movable treatment device (11) configured to treat the target surface (12) and comprising the at least one inertial sensor (13).

14. A method for performing a localization of a movable treatment device (11) relative to a target surface (12), the movable treatment device (11) comprising at least one inertial sensor (13) and being configured to treat the target surface (12), the method comprising:
providing two or more motion classes ($15_1$, $15_2$, $15_3$, ..., $15_k$) contained in a set (15) of motion classes of the movable treatment device (11),
receiving at least one inertial sensor data ($17_1$, $17_2$, $17_3$, ..., $17_n$) from the inertial sensor (13), the at least one inertial sensor data ($17_1$, $17_2$, $17_3$, ..., $17_n$) representing a movement of the movable treatment device (11),
receiving and processing by means of a neural network (18) the at least one inertial sensor data ($17_1$, $17_2$, $17_3$, ..., $17_n$) and classifying the at least one inertial sensor data ($17_1$, $17_2$, $17_3$, ..., $17_n$) with respect to at least one motion class ($15_1$, $15_2$, $15_3$, ..., $15_k$) contained in the set (15) of motion classes, wherein the motion classes ($15_1$, $15_2$, $15_3$, ..., $15_k$) are each associated with one or more different zones ($21_1$, $21_2$, $21_3$, ..., $21_n$) of the target surface (12) so that the classification of the at least one inertial sensor data ($17_1$, $17_2$, $17_3$, ..., $17_n$) with the at least one motion class ($15_1$, $15_2$, $15_3$, ..., $15_k$) indicates an estimation of the location of the movable treatment device (11) with respect to the one or more zones ($21_1$, $21_2$, $21_3$, ..., $21_m$) of the target surface (12),
wherein an output ($y_{t-1}$; $y_t$; $y_{t+1}$) of the neural network (18) comprises one or more probability or likelihood values for the estimation of the location of the movable treatment device (11) with respect to the one or more zones ($21_1$, $21_2$, $21_3$, ..., $21_m$) of the target surface (12),
wherein performance of the method does not use input from a camera.

* * * * *